(12) United States Patent
Li et al.

(10) Patent No.: US 6,399,334 B1
(45) Date of Patent: *Jun. 4, 2002

(54) NORMALIZED NUCLEIC ACID LIBRARIES AND METHODS OF PRODUCTION THEREOF

(75) Inventors: Wu-Bo Li; Paul E. Nisson, both of Gaithersburg; Joel Jessee, Mount Airy, all of MD (US)

(73) Assignee: Invitrogen Corporation, Carlsbad, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 57 days.

(21) Appl. No.: 09/159,496

(22) Filed: Sep. 23, 1998

Related U.S. Application Data

(60) Provisional application No. 60/059,817, filed on Sep. 24, 1997.

(51) Int. Cl.$^7$ .............................. C12P 19/34; C12Q 1/68
(52) U.S. Cl. .......................................... 435/91.1; 435/6
(58) Field of Search .................. 435/6, 91.1, 91.2; 536/23.1

(56) References Cited

U.S. PATENT DOCUMENTS

| | | | |
|---|---|---|---|
| 5,262,311 A | 11/1993 | Pardee et al. .............. | 435/91.2 |
| 5,326,691 A | 7/1994 | Hozier .......................... | 435/6 |
| 5,482,845 A | 1/1996 | Soares et al. .............. | 435/91.1 |
| 5,618,702 A | 4/1997 | Scanlon ..................... | 435/91.2 |
| 5,618,703 A | 4/1997 | Gelfand ..................... | 435/91.2 |
| 5,629,179 A | 5/1997 | Mierendorf et al. ........ | 435/91.2 |
| 5,637,685 A | 6/1997 | Soares et al. .............. | 536/23.1 |
| 5,643,761 A | 7/1997 | Fisher et al. .............. | 435/91.1 |
| 5,681,726 A | 10/1997 | Huse et al. .............. | 435/91.52 |
| 5,726,022 A | 3/1998 | Burmer ......................... | 435/6 |
| 5,759,820 A | 6/1998 | Hornes et al. ............. | 435/91.1 |
| 5,763,239 A | 6/1998 | Short et al. .............. | 435/172.1 |
| 5,830,662 A | 11/1998 | Soares et al. ................... | 435/6 |
| 5,846,721 A | 12/1998 | Soares et al. ................... | 435/6 |
| 6,001,574 A | 12/1999 | Short et al. .................... | 435/6 |

FOREIGN PATENT DOCUMENTS

| | | |
|---|---|---|
| EP | 0 622 457 A1 | 11/1994 |
| EP | 0 645 449 A1 | 3/1995 |
| EP | 0 735 144 A1 | 10/1996 |
| EP | 0 761 822 A2 | 3/1997 |
| EP | 0 872 559 A1 | 10/1998 |
| WO | WO 89/12063 | 12/1989 |
| WO | WO 90/06044 | 6/1990 |
| WO | WO 91/11533 | 8/1991 |
| WO | WO 91/18114 | 11/1991 |
| WO | WO 97/07244 | 2/1997 |
| WO | WO 97/24455 | 7/1997 |
| WO | WO 97/41249 | 11/1997 |
| WO | WO 97/48717 | 12/1997 |
| WO | WO 98/14619 | 4/1998 |

OTHER PUBLICATIONS

Sagerstrom et al. (Ann.Rev.Biochem 66:751–783, 1997.*
Fellman, F., et al., "Simplified Protocol of Solid–Phase cDNA Libraries for Multiple PCR Amplification," *BioTechniques* 21:766–770 (Nov. 1996).
Hara, E., et al., "Subtractive cDNA cloning using oligo (dT)$_{30}$–latex and PCR: isolation of cDNA clones specific to undifferentiated human embryonal carcinoma cells," *Nucl. Acids Res.* 19:7097–7104 (1991).
Lambert, K.N., and Williamson, V.M., "cDNA library construction from small amounts of RNA using paramagnetic beads and PCR," *Nucl. Acids Res.* 21:775–776 (1993).
Rainieri, I., et al., "Improved efficiency for single–sided PCR by creating a reusable pool of first–strand cDNA coupled to a solid phase," *Nucl. Acids Res.* 19:4010 (1991).
Carninci, P., et al., "High–Efficiency Full–Length cDNA Cloning by Biotinylated CAP Trapper," *Genomics* 37:327–336, Academic Press, Inc. (Nov. 1996).
Gerard, G.F., "Reverse Transcriptase: A Historical Perspective," *FOCUS* 20(3):65–67, Life Technologies, Inc. (Fall 1998).
Kuribayashi–Ohta, K., et al., "Application of oligo (dT)$_{30}$–latex for rapid purificaton of poly(A)$^+$ mRNA and for hybrid subtraction with the in situ reverse transcribed cDNA," *Biochim. Biophys. Acta* 1156:204–212, Elsevier Science Publishers B.V. (1993).
Luqmani, Y.A., and Lymboura, M., "Subtraction Hybridization Cloning of RNA Amplified from Different Cell Populations Microdissected from Cryostat Tissue Sections," *Anal. Biochem.* 222:102–109, Academic Press, Inc. (1994).
Mészáros, M., and Morton, D.B., "Subtractive Hybridization Strategy Using Paramagnetic Oligo (dT) Beads and PCR," *BioTechniques* 20:413–419, Eaton Publishing Co. (Mar. 1996).
Sasaki, Y.F., et al., "Construction of a normalized cDNA library by introduction of a semi solid mRNA–cDNA hybridization system," *Nucl. Acids Res.* 22:987–992, Oxford Univ. Press (1994).

(List continued on next page.)

*Primary Examiner*—Eggerton A. Campbell
(74) *Attorney, Agent, or Firm*—Sterne, Kessler, Goldstein & Fox P.L.L.C.

(57) ABSTRACT

The present invention relates generally to methods for producing normalized nucleic acid libraries in which each member of the library can be isolated with approximately equivalent probability. In particular, the present methods comprise subtractive hybridization of a nucleic acid library with haptenylated (e.g., biotinylated, avidinated or streptavidinated) nucleic acid molecules that are complementary to one or more of the nucleic acid molecules of the library, such that the variation in the abundances of the individual nucleic acid molecules in the library is reduced. The invention also relates to production of normalized nucleic acid libraries (particularly cDNA libraries) in which contaminating nucleic acid molecules have been reduced or eliminated, and to normalized nucleic acid libraries produced by such methods.

52 Claims, 7 Drawing Sheets

OTHER PUBLICATIONS

Thomas, M.G., et al., "Sequencing of cDNA using anchored oligo dT primers," *Nucl. Acids Res.* 21:3915–3916, Oxford Univ. Press (1993).

Dialog File 351 (Derwent World Patents Index), unverified English language abstract for European Patent Office Publication No. EP 0 645 449 A1 (Doc. No. A02), Derwent WPI Accession No. 1995–124590/199517 (1995).

de Fatima Donaldo, M., et al., "Normalization and Subtraction: Two Approaches to Facilitate Gene Discovery," *Genome Res.* 6:791–806 (Sep. 1996).

Britten, R.J., et al., "Analysis of Repeating DNA Sequences by Reassociation," *Meth. Enzymol.* 29:363–418 (1974).

Ko, M.S.H., "An 'equalized cDNA library' by the reassociation of short double–stranded cDNAs," *Nucl. Acids Res.* 18:5705–5711 (Oct. 1990).

Langer, P.R., et al., "Enzymatic synthesis of biotin–labeled polynucleotides: Novel nucleic acid affinity probes," *Proc. Natl. Acad. Sci. USA* 78:6633–6637 (Nov. 1981).

Li, W.–B., et al., "The Isolation of Differentially Expressed Genes in Fibroblast Growth Factor Stimulated $BC_3H1$ Cells by Subtractive Hybridization," *BioTechniques* 16:722–729 (1994).

Patanjali, S.R., et al., "Construction of a uniform–abundance (normalizaed) cDNA library," *Proc. Natl. Acad. Sci. USA* 88:1943–1947 (Mar. 1991).

Soares, M.B., et al., "Construction and characterization of a normalized cDNA library," *Proc. Natl. Acad. Sci. USA* 91: 9228–9232 (Sep. 1994).

Van Gelder, R.N.., et al., "Amplified RNA synthesized from limited quantities of heterogeneous cDNA," *Proc. Natl. Acad. Sci. USA* 87:1663–1667 (Mar. 1990).

Fargnoli, J., et al., "Low–Ratio Hybridization Subtraction," *Anal. Biochem.* 187:364–373 (Jun. 1990).

Nozaki, M., et al., "Isolation of endo A cDNA from mouse 8–cell stage embryos," *Biochem. Biophys. Res. Comm.* 154:890–894 (Aug. 1988).

\* cited by examiner

Production of a normalized cDNA library by subtraction with a biotinylated RNA driver 1 Selection with 3'-biotin-oligodA-NotI
2 5-methylcytosine repair synthesis/HhaI digestion

NORMALIZED NUCLEIC ACID LIBRARIES AND METHODS OF PRODUCTION THEREOF

CROSS REFERENCE TO RELATED APPLICATION

The present application claims the benefit of the filing date of U.S. Provisional Application No. 60/059,817, filed Sep. 24, 1997, the disclosure of which is incorporated by reference herein in its entirety.

FIELD OF THE INVENTION

The present invention is in the fields of molecular biology and genetics. The invention relates generally to methods for producing normalized nucleic acid libraries, such that the variation in the abundance of the individual nucleic acid molecules in the library is substantially reduced (e.g., to no greater than about two orders of magnitude). The invention also relates to normalized libraries produced by these methods, to nucleic acid molecules isolated from these libraries, to genetic constructs (e.g., vectors) comprising these nucleic acid molecules, and to host cells comprising such normalized libraries.

BACKGROUND OF THE INVENTION

The elucidation of the mechanisms that dictate the normal functioning of living cells requires a detailed understanding of the information encoded in all of the genes (also referred to here synonymously as the genome). To map and sequence the genes contained in the genomes of different organisms, messenger RNA (mRNA) sequences, which are representative of the genes of the genome, are typically used to evaluate the genetic make up of the particular cell or organism of interest. However, the mRNAs (estimated to number 100,000 in human) are produced at different levels within different cell types at different points in development (e.g., there are less than one copy per cell of some mRNAs and there are millions of copies per cell of others). These mRNAs, their developmental and cell-type specific regulated expression, and their translation into protein is what produces the unique character of a particular cell type. For example, adult muscle cells produce high levels of myoglobin mRNA whereas mature red blood cells contain high levels of hemoglobin. In the fetus, hemoglobin is produced by the liver; however, following birth, the type of hemoglobin produced and the tissue source both change, due to changes in gene expression.

An understanding of the molecular details of normal functioning of cells is essential in order to understand and treat inherited diseases where the regulation and expression of one or more genes may have changed. Integral to this goal is the production of libraries of cloned nucleic acids from which all or substantially all of the members of the libraries can be isolated with approximately equal probability.

A normalized library with a lower range of its members relative concentrations, for example as low as about 2–4 fold, would have the advantage of making essentially all of the mRNAs available for isolation and subsequent analysis. This type of library would further the understanding of the normal function of individual genes and the genome in general. However, none of the methods reported heretofore have resulted in the production of normalized nucleic acid libraries where essentially all of the nucleic acid molecules or genes expressed in a particular cell or tissue type are represented and can be isolated with high probability. Although some investigators have attempted to normalize (i.e., reduce the variation in the relative abundance of the components of the population of nucleic acid molecules), none have been successful at bringing the relative abundance of the total population to within a range of two orders of magnitude (Bonaldo, M., Lennon, G., Soares, M. B., *Genome Res.* 6:791–866 (1996); Ko, M. S. H., *Nucl. Acids Res.* 18:5705–5711 (1990); Pantanjali, S. R., et al., *Proc. Natl. Acad. Sci. USA* 88:1943–1947 (1991); Soares, M. B., *Proc. Natl. Acad. Sci. USA* 91:9228–9232 (1994)). The resulting "normalized" libraries have failed to provide the quantity of novel information needed to understand the expression of most genes. Thus, there exists a current need for methods of producing normalized nucleic acid libraries, and for normalized nucleic acid libraries produced by such methods.

BRIEF SUMMARY OF THE INVENTION

The present invention meets this need by providing methods for producing normalized nucleic acid libraries (i.e., libraries of cloned nucleic acid molecules from which each member nucleic acid molecule can be isolated with approximately equivalent probability). In particular, the invention relates to methods for normalization of a nucleic acid library, which may be a single-stranded or double-stranded cDNA library, comprising:

(a) synthesizing one or more nucleic acid molecules complementary to all or a portion of the nucleic acid molecules of the library, wherein the synthesized nucleic acid molecules comprise at least one hapten, thereby producing haptenylated nucleic acid molecules (which may be RNA molecules or DNA molecules);

(b) incubating a nucleic acid library to be normalized with the haptenylated nucleic acid molecules (e.g. also referred to as driver) under conditions favoring the hybridization of the more highly abundant molecules of the library with the haptenylated nucleic acid molecules; and (c) removing the hybridized molecules, thereby producing a normalized library.

In a preferred aspect of the invention, the relative concentration of all members of the normalized library are within one to two orders of magnitude. In another preferred aspect, the invention allows removal or elimination of contaminating nucleic acid molecule from the normalized library. Such contamination may include vectors within the library which do not contain inserts (e.g. background). In this manner, all or a substantial portion of the normalized library will comprise vectors containing inserted nucleic acid molecules of the library.

The invention also relates to such methods wherein the conditions favoring hybridization of the more highly abundant molecules of the library with the haptenylated molecules are selected from the group consisting of. (a) a COT equal to or greater than 25; (b) a COT equal to or greater than 50; (c) a COT equal to or greater than 100; (d) a COT equal to or greater than 1,000; (e) a COT equal to or greater than 2,000; (f) a COT equal to or greater than 5,000; (g) a COT from about 10 to 10,000; (h) a COT from about 25 to 10,000; (i) a COT from about 50 to 10,000; (j) a COT from about 1,000 to 10,000; (k) a COT from about 5,000 to 10,000; (l) a COT from about 500 to 5,000; (m) a COT from about 100 to 1000; and (n) a COT of less than 10,000.

In a preferred aspect of the invention, a population of mRNA is incubated under conditions sufficient to produce a population of cDNA molecules complementary to all or a portion of said mRNA molecules. Preferable, such a population of cDNA molecules (e.g. single stranded cDNA) is produced by mixing the population of mRNA molecules (template molecules) with one or more polypeptides having reverse transcriptase activity and incubating said mixture under conditions sufficient to produce a population of single stranded cDNA molecules complementary to all or a portion of said mRNA molecules. The single stranded cDNA molecules may then be used as template molecules to make double stranded cDNA molecules by incubating the mixture under appropriate conditions in the presence of one or more DNA polymerases. The resulting population of double-stranded or single-stranded cDNA libraries may be normalized in accordance with the invention. Preferably, such cDNA libraries are inserted into one or more vectors prior to normalization. Alternatively, the cDNA libraries may be normalized prior to insertion within one or more vectors, and after normalization may be cloned into one or more vectors.

In a particularly preferred aspect of the invention, the library to be normalized is contained in (inserted in) one or more vectors, which may be a plasmid, a cosmid, a phagemid and the like. Such vectors preferably comprise one or more promoters which allow the synthesis of at least one RNA molecule from all or a portion of the nucleic acid molecules (preferably cDNA molecules) inserted in the vector. Thus, by use of the promoters, haptenylated RNA molecules complementary to all or a portion of the nucleic acid molecules of the library may be made and used to normalize the library in accordance with the invention. Such synthesized RNA molecules (which have been haptenylated) will be complementary to all or a portion of the vector inserts of the library. More highly abundant molecules in the library may then be preferentially removed by hybridizing the haptenylated RNA molecules to the library, thereby producing the normalized library of the invention. Without being limited, the synthesized RNA molecules are thought to be representative of the library; that is, more highly abundant species in the library result in more highly abundant haptenylated RNA using the above method. The relative abundance of the molecules within the library, and therefore, within the haptenylated RNA determines the rate of removal of particular species of the library; if a particular species abundance is high, such highly abundant species will be removed more readily while low abundant species will be removed less readily from the population. Normalization by this process thus allows one to substantially equalize the level of each species within the library.

In another preferred aspect of the invention, the library to be normalized need not be inserted in one or more vectors prior to normalization. In such aspect of the invention, the nucleic acid molecules of the library may be used to synthesize haptenylated nucleic acid molecules using well known techniques. For example, haptenylated nucleic acid molecules may be synthesized in the presence of one or more DNA polymerases, one or more appropriate primers or probes and one or more nucleotides (the nucleotides and/or primers or probes may be haptenylated). In this manner, haptenylated DNA molecules will be produced and may be used to normalized the library in accordance with the invention. Alternatively, one or more promoters may be added to (or ligated to) the library molecules, thereby allowing synthesis of haptenylated RNA molecules for use to normalize the library in accordance with the invention. For example, adapters containing one or more promoters are added to (ligated to) one or more ends of double stranded library molecules (e.g. cDNA library prepared from a population of mRNA molecules). Such promoters may then be used to prepare haptenylated RNA molecules complementary to all or a portion of the nucleic acid molecules of the library. In accordance with the invention, the library may then be normalized and, if desired, inserted into one or more vectors.

While haptenylated RNA is preferably used to normalize libraries, other haptenylated nucleic acid molecules may be used in accordance with the invention. For example, haptenylated DNA may be synthesized from the library and used in accordance with the invention.

Haptens suitable for use in the methods of the invention include, but are not limited to, avidin, streptavidin, protein A, protein G, a cell-surface Fc receptor, an antibody-specific antigen, an enzyme-specific substrate, polymyxin B, endotoxin-neutralizing protein (ENP), $Fe^{+++}$, a transferrin receptor, an insulin receptor, a cytokine receptor, CD4, spectrin, fodrin, ICAM-1, ICAM-2, C3bi, fibrinogen, Factor X, ankyrin, an integrin, vitronectin, fibronectin, collagen, laminin, glycophorin, Mac-1, LFA-1, β-actin, gp120, a cytokine, insulin, ferrotransferrin, apotransferrin, lipopolysaccharide, an enzyme, an antibody, biotin and combinations thereof. A particularly preferred hapten is biotin.

In accordance with the invention, hybridized molecules produced by the above-described methods may be isolated, for example by extraction or by hapten-ligand interactions. Preferably, extraction methods (e.g. using organic solvents) are used. Isolation by hapten-ligand interactions may be accomplished by incubation of the haptenylated molecules with a solid support comprising at least one ligand that binds the hapten. Preferred ligands for use in such isolation methods correspond to the particular hapten used, and include, but are not limited to, biotin, an antibody, an enzyme, lipopolysaccharide, apotransferrin, ferrotransferrin, insulin, a cytokine, gp120, β-actin, LFA- 1, Mac-1, glycophorin, laminin, collagen, fibronectin, vitronectin, an integrin, ankyrin, C3bi, fibrinogen, Factor X, ICAM-1, ICAM-2, spectrin, fodrin, CD4, a cytokine receptor, an insulin receptor, a transferrin receptor, $Fe^{+++}$, polymyxin B, endotoxin-neutralizing protein (ENP), an enzyme-specific substrate, protein A, protein G, a cell-surface Fc receptor, an antibody-specific antigen, avidin, streptavidin or combinations thereof. The solid support used in these isolation methods may be nitrocellulose, diazocellulose, glass, polystyrene, polyvinylchloride, polypropylene, polyethylene, dextran, Sepharose, agar, starch, nylon, a latex bead, a magnetic bead, a paramagnetic bead, a superparamagnetic bead or a microtitre plate. Preferred solid supports are magnetic beads, paramagnetic beads and superparamagnetic beads, and particularly preferred are such beads comprising one or more streptavidin or avidin molecules.

In another aspect of the invention, normalized libraries are subjected to further isolation or selection steps which allow removal of unwanted contamination or background. Such contamination or background may include undesirable nucleic acids. For example, when a library to be normalized is constructed in one or more vectors, a low percentage of vector (without insert) may be present in the library. Upon normalization, such low abundance molecules (e.g. vector background) may become a more significant constituent as a result of the normalization process. That is, the relative level of such low abundance background may be increased as part of the normalization process.

Removal of such contaminating nucleic acids may be accomplished by incubating a normalized library with one or more haptenylated probes which are specific for the nucleic acid molecules of the library (e.g. target specific probes). In principal, removal of contaminating sequences can be accomplished by selecting those nucleic acids having the sequence of interest or by eliminating those molecules that do not contain sequences of interest. In accordance with the invention, removal of contaminating nucleic acid molecules may be performed on any normalized library (whether or not the library is constructed in a vector). Thus, the probes will be designed such that they will not recognize or hybridize to contaminating nucleic acids (as in the preferred embodiment using the oligodA-NotI 3' biotin probe). Upon hybridization of the haptenylated probe with nucleic acid molecules of the library, the haptenylated probes will bind to and select desired sequences within the normalized library and leave behind contaminating nucleic acid molecules, resulting in a selected normalized library. The selected normalized library may then be isolated. In a preferred aspect, such isolated selected normalized libraries are single-stranded, and may be made double stranded following selection by incubating the single-stranded library under conditions sufficient to render the nucleic acid molecules double-stranded. The double stranded molecules may then be transformed into one or more host cells. Alternatively, the normalized library may be made double stranded using the haptenylated probe or primer (preferably target specific) and then selected by extraction or ligand-hapten interactions. Such selected double stranded molecules may then be transformed into one or more host cells.

In another aspect of the invention, contaminating nucleic acids may be reduced or eliminated by incubating the normalized library in the presence of one or more primers specific for library sequences (specific for insert-containing clones, e.g. oligodA-NotI). This aspect of the invention may comprise incubating the single stranded normalized library with one or more nucleotides (preferably nucleotides which confer nuclease resistance to the synthesized nucleic acid molecules), and one or more polypeptides having polymerase activity, under conditions sufficient to render the nucleic acid molecules double-stranded. The resulting double stranded molecules may then be transformed into one or more host cells. Alternatively, resulting double stranded molecules containing nucleotides which confer nuclease resistance may be digested with such a nuclease and transformed into one or more host cells.

In yet another aspect, the elimination or removal of contaminating nucleic acid may be accomplished prior to normalization of the library, thereby resulting in selected normalized library of the invention. In such a method, the library to be normalized may be subjected to any of the methods described herein to remove unwanted nucleic acid molecules and then the library may then be normalized by the process of the invention to provide for the selected normalized libraries of the invention.

In accordance with the invention, double stranded nucleic acid molecules are preferably made single stranded before hybridization. Thus, the methods of the invention may further comprise treating the above-described double-stranded nucleic acid molecules of the library under conditions sufficient to render the nucleic acid molecules single-stranded. Such conditions may comprise degradation of one strand of the double-stranded nucleic acid molecules (preferably using gene II protein and Exonuclease III), or denaturing the double-stranded nucleic acid molecules using heat, alkali and the like.

The invention also relates to normalized nucleic acid libraries, selected normalized nucleic acid libraries and transformed host cells produced by the above-described methods.

Other preferred embodiments of the present invention will be apparent to one of ordinary skill in light of the following drawings and description of the invention, and of the claims.

DETAILED DESCRIPTION OF THE INVENTION

Definitions

Figure 1:
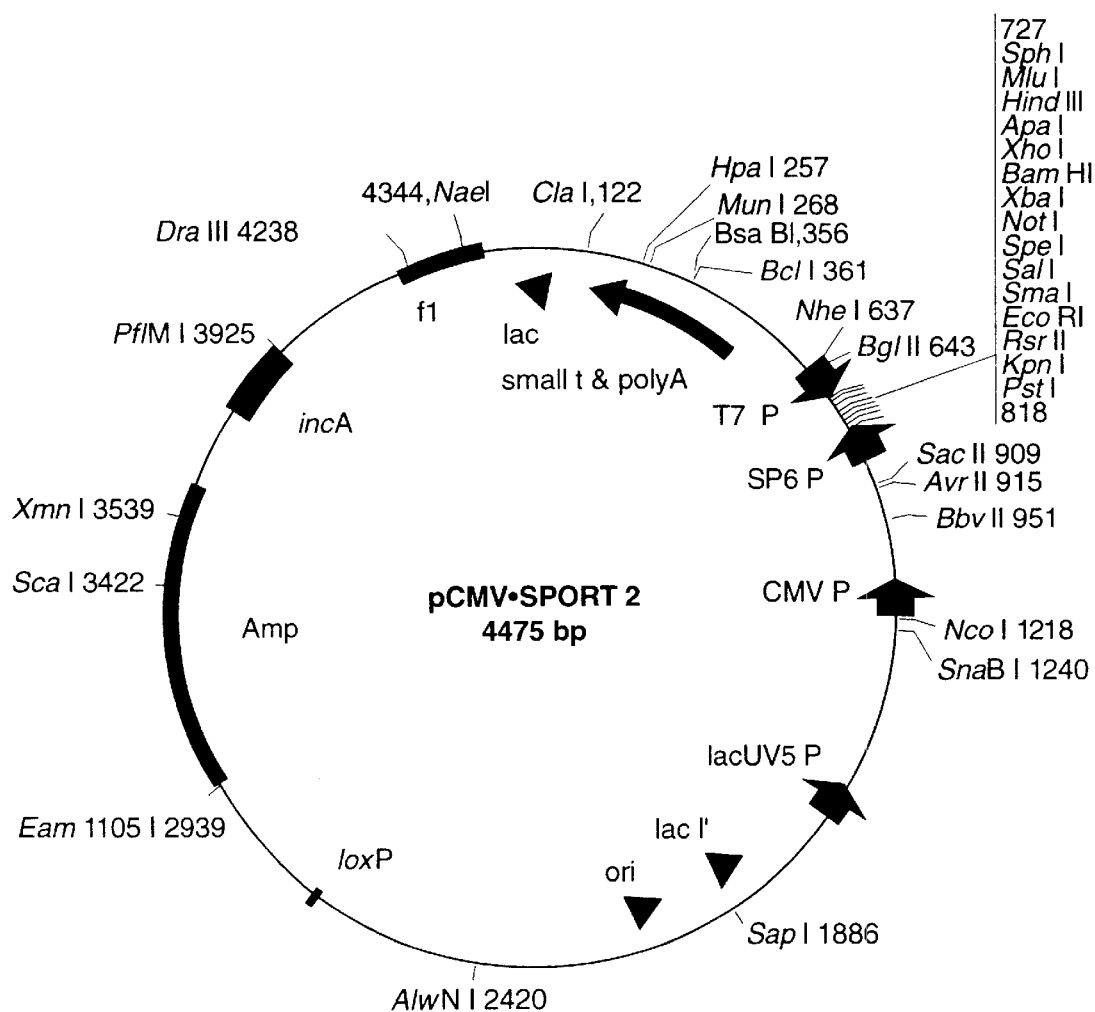
FIG. 1 is a schematic of the phagemid that has been used to construct a directionally cloned cDNA library.

In the description that follows, a number of terms used in recombinant DNA technology are utilized extensively. In order to provide a clearer and consistent understanding of the specification and claims, including the scope to be given such terms, the following definitions are provided.

Library. As used herein, the term "library" or "nucleic acid library" means a set of nucleic acid molecules (circular or linear) representative of all or a significant portion of the DNA content of an organism (a "genomic library"), or a set of nucleic acid molecules representative of all or a significant portion of the expressed genes (a "cDNA library") in a cell, tissue, organ or organism. Such libraries may or may not be contained in one or more vectors.

Normalized. As used herein, the term "normalized" or "normalized library" means a nucleic acid library that has been manipulated, preferably using the methods of the invention, to reduce the relative variation in abundance among member nucleic acid molecules in the library to a range of no greater than about 25-fold, no greater than about 20-fold, no greater than about 15-fold, no greater than about 10-fold, no greater than about 7-fold, no greater than about 6-fold, no greater than about 5-fold, no greater than about 4-fold, no greater than about 3-fold or no greater than about 2-fold.

Driver. As used herein, the term "driver" refers to a population of nucleic acid molecules (preferably RNA) which are complementary to all or a portion of nucleic acid molecules of a library. Such driver preferably comprises one or more haptens and preferably are in molar excess (greater than 10, preferably greater than 20 fold) compared to the library of interest. In accordance with the invention, the driver is preferably synthesized from the library to be normalized and then the driver is used to normalize that library.

Background. As used herein, background refers to contaminating nucleic acid molecules which may be present in a constructed library. Typical contaminating nucleic acid molecules are vectors in which the library has been constructed but which have lost the inserted nucleic acid molecule (by deletion or otherwise) or which do not contain nucleic acid inserts. The target specific probes or primers described herein will not hybridize to contaminating or background sequences.

Vector. As used herein, a "vector" is a plasmid, cosmid, phagemid or phage DNA or other DNA molecule which is able to replicate autonomously in a host cell, and which is characterized by one or a small number of restriction endonuclease recognition sites at which such DNA sequences may be cut in a determinable fashion without loss of an essential biological function of the vector, and into which DNA may be inserted in order to bring about its replication and cloning. The vector may further contain a marker suitable for use in the identification of cells transformed with the vector. Markers, for example, include but are not limited to tetracycline resistance or ampicillin resistance.

Primer. As used herein, "primer" refers to a single-stranded oligonucleotide that is extended by covalent bonding of nucleotide monomers during amplification or polymerization of a DNA molecule.

Probe. As used herein, "probe" refers to a single stranded oligonucleotide that may be used to hybridize and/or isolate one or more nucleic acid molecules of interest. Such probes may or may not comprise one or more haptens.

Template. The term "template" as used herein refers to a double-stranded or single-stranded nucleic acid molecules which are to be amplified, synthesized or sequenced. In the case of a double-stranded molecules, denaturation of its strands to form a first and a second strand is preferably performed before these molecules may be amplified, synthesized or sequenced, or the double stranded molecule may be used directly as a template. For single stranded templates, a primer, complementary to a portion of the template is hybridized under appropriate conditions and one or more polymerases may then synthesize a nucleic acid molecule complementary to all or a portion of said template. Alternatively, for double stranded templates, one or more promoters (e.g. promoter) may be used in combination with one or more polymerases to make nucleic acid molecules complementary to all or a portion of the template. The newly synthesized molecules, according to the invention, may be equal or shorter in length than the original template.

Incorporating. The term "incorporating" as used herein means becoming a part of a DNA and/or RNA molecule or primer.

Amplification. As used herein "amplification" refers to any in vitro method for increasing the number of copies of a nucleotide sequence with the use of a polymerase. Nucleic acid amplification results in the incorporation of nucleotides into a DNA and/or RNA molecule or primer thereby forming a new molecule complementary to a template. The formed nucleic acid molecule and its template can be used as templates to synthesize additional nucleic acid molecules. As used herein, one amplification reaction may consist of many rounds of replication. DNA amplification reactions include, for example, polymerase chain reactions (PCR). One PCR reaction may consist of 5 to 100 "cycles" of denaturation and synthesis of a DNA molecule.

Oligonucleotide. "Oligonucleotide" refers to a synthetic or natural molecule comprising a covalently linked sequence of nucleotides which are joined by a phosphodiester bond between the 3' position of the deoxyribose or ribose of one nucleotide and the 5' position of the deoxyribose or ribose of the adjacent nucleotide. A blocking oligonucleotide refers to oligonucleotides which are used to prevent hybridization of a nucleic acid molecules (e.g. probe or a primer) to unwanted or undesired molecules. For example, the blocking oligonucleotide may prevent the 5' and in some cases the 3' end sequences of the driver components from hybridizing to the library vector.

Nucleotide. As used herein "nucleotide" refers to abase-sugar-phosphate combination. Nucleotides are monomeric units of a nucleic acid sequence (DNA and RNA). The term nucleotide includes ribonucleoside triphosphate ATP, UTP, CTP, GTP and deoxyribonucleoside triphosphates such as dATP, dCTP, dITP, dUTP, dGTP, dTTP, or derivatives thereof. Such derivatives include, for example, [$\alpha$S]dATP, 7-deaza-dGTP and 7-deaza-dATP, and nucleotide derivatives that confer nuclease resistance on the nucleic acid molecule containing them. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. According to the present invention, a "nucleotide" may be unlabeled or detectably labeled by well known techniques. Detectable labels include, for example, radioactive isotopes, fluorescent labels, chemiluminescent labels, bioluminescent labels and enzyme labels.

Hybridization. The terms "hybridization" and "hybridizing" refers to base pairing of two complementary single-stranded nucleic acid molecules (RNA and/or DNA) to give a double-stranded molecule. As used herein, two nucleic acid molecules may be hybridized, although the base pairing is not completely complementary. Accordingly, mismatched bases do not prevent hybridization of two nucleic acid molecules provided that appropriate conditions, well known in the art, are used. In the present invention, the term "hybridization" refers particularly to hybridization of a driver to the library to be normalized. Other terms used in the fields of recombinant DNA technology and molecular and cell biology as used herein will be generally understood by one of ordinary skill in the applicable arts.

Overview

The present invention is generally directed to methods for producing normalized nucleic acid libraries, and to normalized libraries produced by these methods. In one preferred embodiment of the invention, the normalized library produced is a cDNA library, which may be single-stranded or double-stranded. According to the invention, normalization of a nucleic acid library is accomplished using haptenylated nucleic acid molecules (i.e., nucleic acid molecules having covalently coupled thereto one or more hapten molecules, such as those described below) which will hybridize more rapidly to the more highly abundant nucleic acid molecules of the library. Such haptenylated nucleic acid molecules are referred to as a driver. This hybridization forms complexes of nucleic acid molecules which may then be removed (thereby reducing the abundance of the bound nucleic acid molecules in the library), preferably via ligand-hapten interactions or by extraction techniques. It has been discovered that, by the methods of the invention, normalized nucleic acid libraries having a maximum variation in abundance of the member nucleic acid molecules no greater than about 2- to about 10-fold may be produced. Moreover, the methods of the invention provide normalized libraries which have significantly reduced background. Thus, the invention provides methods for producing nucleic acid libraries, particularly cDNA libraries, from which each member nucleic acid molecule can be isolated with approximately equivalent probability, regardless of its copy number in the original library.

Sources of Nucleic Acid Libraries

Using the methods of the invention, normalized nucleic acid libraries, particularly normalized cDNA libraries, may be prepared from a variety of nucleic acid libraries. Such libraries to be normalized may be prepared using standard techniques or may be obtained commercially (Life Technologies, Inc., Rockville, Md.). Nucleic acid libraries for use in the present invention include those comprising populations of single-stranded or double-stranded nucleic acid molecules, or preferably populations of single-stranded or double-stranded DNA molecules. More preferred nucleic acid libraries to be normalized in accordance with the invention include those comprising complementary DNA (cDNA) libraries. Such cDNA libraries (double stranded or single stranded) may be made using well known techniques using messenger RNA or polyA+ RNA or may be obtained commercially, for example from Life Technologies, Inc. (Rockville, Md.), or other commercial sources that will be familiar to one of ordinary skill. cDNA libraries used in accordance with the invention are preferably made with reverse transcriptases having substantially reduced RNase H activity (see below). The pCMVSPORT vectors for library construction is preferred and Life Technologies, Inc. (Rockville, Md.) cDNA libraries are housed in these vectors. In a preferred aspect of the invention, the nucleic acid molecules of the library may be contained in one or more vectors, such as plasmids, cosmids or phages.

In accordance with the invention, the nucleic acid libraries may be prepared from populations of nucleic acid molecules obtained from natural sources, such as a variety of cells, tissues, organs or organisms. Cells that may be used as sources of nucleic acid molecules may be prokaryotic (bacterial cells, including those of species of the genera Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium, and Streptomyces) or eukaryotic (including fungi (especially yeasts), plants, protozoans and other parasites, and animals including insects (particularly Drosophila spp. cells), nematodes (particularly *Caenorhabditis elegans cells*), and mammals (particularly human cells)).

Mammalian somatic cells that may be used as sources of populations or libraries of nucleic acids include blood cells (reticulocytes and leukocytes), endothelial cells, epithelial cells, neuronal cells (from the central or peripheral nervous systems), muscle cells (including myocytes and myoblasts from skeletal, smooth or cardiac muscle), connective tissue cells (including fibroblasts, adipocytes, chondrocytes, chondroblasts, osteocytes and osteoblasts) and other stromal cells (e.g., macrophages, dendritic cells, Schwann cells). Mammalian germ cells (spermatocytes and oocytes) may also be used as sources of nucleic acids or libraries for use in the invention, as may the progenitors, precursors and stem cells that give rise to the above somatic and germ cells. Also suitable for use as nucleic acid sources are mammalian tissues or organs such as those derived from brain, kidney, liver, pancreas, blood, bone marrow, muscle, nervous, skin, genitourinary, circulatory, lymphoid, gastrointestinal and connective tissue sources, as well as those derived from a mammalian (including human) embryo or fetus.

Any of the above prokaryotic or eukaryotic cells, tissues and organs may be normal, diseased, transformed, established, progenitors, precursors, fetal or embryonic. Diseased cells may, for example, include those involved in infectious diseases (caused by bacteria, fungi or yeast, viruses (including HIV) or parasites), in genetic or biochemical pathologies (e.g., cystic fibrosis, hemophilia, Alzheimer's disease, muscular dystrophy or multiple sclerosis) or in cancerous processes. Transformed or established animal cell lines may include, for example, COS cells, CHO cells, VERO cells, BHK cells, HeLa cells, HepG2 cells, K562 cells, F9 cells and the like. Other cells, cell lines, tissues, organs and organisms suitable as sources of nucleic acids for use in the present invention will be apparent to one of ordinary skill in the art. These cells, tissues, organs and organisms may be obtained from their natural sources, or may be obtained commercially from sources such as American Type Culture Collection (Rockville, Md.) and others that are known to the skilled artisan.

Once the starting cells, tissues, organs or other samples are obtained, nucleic acid molecules (such as mRNA or poly A+ RNA) may be isolated, and nucleic acid libraries (such as cDNA libraries) prepared therefrom, by methods that are well-known in the art (See, e.g., Maniatis, T., et al., *Cell* 15:687–701 (1978); Okayama, H., and Berg, P., *Mol. Cell. Biol.* 2:161–170 (1982); Gubler, U., and Hoffman, B. J., *Gene* 25:263–269 (1983)). As noted above, nucleic acid libraries prepared in such a manner will typically contain a vast range of abundances of member nucleic acid molecules, depending upon the cell, tissue or organism source, and the stage of development or cell cycle of the source. The methods of the invention may then be used to normalize, or narrow or reduce the relative abundances of nucleic acid molecules in the nucleic acid library.

Production of Normalized Nucleic Acid Libraries

In the practice of the invention, nucleic acid libraries are normalized, to produce normalized nucleic acid libraries, by methods that may comprise one or more steps. One preferred method of the invention may comprise, for example:

(a) synthesizing one or more nucleic acid molecules complementary to all or a portion of the nucleic acid molecules of the library, wherein the synthesized nucleic acid molecules comprise at least one hapten, thereby producing haptenylated nucleic acid molecules (e.g. driver);

(b) incubating a nucleic acid library to be normalized with the haptenylated nucleic acid molecules under conditions favoring the hybridization of the more highly abundant molecules of the library with the haptenylated nucleic acid molecules; and (c) removing the hybridized molecules, thereby producing a normalized library.

According to the invention, haptenylated nucleic acid molecules complementary to all or a portion of the nucleic acid molecules of the library may be produced, for example, by incubating the nucleic acid molecules of the library with at least one polypeptide having nucleic acid polymerase activity and with at least one nucleotide comprising at least one hapten. If one or more primers are used for synthesis, the primers may comprise one or more haptens to produce the haptenylated nucleic acid molecules (without or with the use of haptenylated nucleotides during synthesis). Preferred polypeptides having nucleic acid polymerase activity for use in this aspect of the invention include those having reverse transcriptase activity and those having DNA polymerase or RNA polymerase activity.

Preferred polypeptides having reverse transcriptase activity (i.e., those polypeptides able to catalyze the synthesis of a DNA molecule from an RNA template) include, but are not limited to, Moloney Murine Leukemia Virus (M-MLV) reverse transcriptase, Rous Sarcoma Virus (RSV) reverse transcriptase, Avian Myeloblastosis Virus (AMV) reverse transcriptase, Rous Associated Virus (RAV) reverse transcriptase, Myeloblastosis Associated Virus (MAV) reverse transcriptase, Human Immunodeficiency Virus (HIV) reverse transcriptase, retroviral reverse transcriptase, retrotransposon reverse transcriptase, hepatitis B reverse transcriptase, cauliflower mosaic virus reverse transcriptase and bacterial reverse transcriptase. Particularly preferred are those polypeptides having reverse transcriptase activity that are also substantially reduced in RNase H activity (i.e., "RNASE H−" polypeptides). By a polypeptide that is "substantially reduced in RNASE H activity" is meant that the polypeptide has less than about 20%, more preferably less than about 15%, 10% or 5%, and most preferably less than about 2%, of the RNASE H activity of a wildtype or RNASE H+ enzyme such as wildtype M-MLV reverse transcriptase. The RNASE H activity may be determined by a variety of assays, such as those described, for example, in U.S. Pat. No. 5,244,797, in Kotewicz, M. L., et al., *Nucl. Acids Res.* 16:265 (1988) and in Gerard, G. F., et al., *FOCUS* 14(5):91 (1992), the disclosures of all of which are fully incorporated herein by reference. Suitable RNASE H− polypeptides for use in the present invention include, but are not limited to, M-MLV H− reverse transcriptase, RSV H− reverse transcriptase, AMV H− reverse transcriptase, RAV H− reverse transcriptase, MAV H− reverse transcriptase, HIV H− reverse transcriptase, and SUPERSCRIPT™ I reverse transcriptase and SUPERSCRIPT™ II reverse transcriptase which are available commercially, for example from Life Technologies, Inc. (Rockville, Md.).

Other polypeptides having nucleic acid polymerase activity suitable for use in the present methods include thermophilic DNA polymerases such as DNA polymerase I, DNA polymerase III, Klenow fragment, T7 polymerase, and T5 polymerase, and thermostable DNA polymerases including, but not limited to, *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (Tli or VENT®) DNA polymerase, *Pyrococcus furiosus* (Pfu or DEEPVENT®) DNA polymerase, *Pyrococcus woosii* (Pwo) DNA polymerase, *Bacillus sterothermophilus* (Bst) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, and mutants, variants and derivatives thereof.

RNA polymerases preferably used in the invention may include SP6 RNA polymerase, T7 RNA polymerase, T3 RNA polymerase and the like. With the use of RNA polymerases, one or more promoters (e.g. SP6 promoter, T7 promoter, etc.) are typically used. For example, double stranded DNA molecules (or double stranded library) containing one or more promoters are used in combination with one or more RNA polymerases to make haptenylated RNA molecules complementary to all or a portion of the double stranded library template. Preferably, such RNA molecules are in large molar excess compared to the templates. In accordance with the invention, such promoters may be provided by the vector in which the library molecules are cloned or by adapter molecules (e.g. double stranded oligonucleotides) which are added to the library molecules. When using such adapter molecules, the adapters (which preferably comprise one or more promoters) are added to the library molecules. Preferably, the library molecules are double stranded linear molecules (e.g. double stranded linear cDNA produced after first and second synthesis), and the adapters may be added using standard techniques (e.g. ligases) to one or both termini of such molecules.

Preferred nucleotides for use in the methods of the present invention include, but are not limited to, ribonucleoside triphosphates such as ATP, UTP, CTP, GTP and derivatives thereof, and deoxyribonucleoside triphosphates such as dATP, dCTP, dITP, dUTP, dGTP, dTTP, or derivatives thereof. Such derivatives include [$\alpha$S]dATP, 7-deaza-dGTP and 7-deaza-dATP, or the corresponding ribonucleoside triphosphates in which deoxyribose has been replaced by ribose. According to the invention, the nucleotides or derivatives thereof preferably comprise one or more hapten molecules covalently bound thereto.

Preferred hapten molecules for use in these methods include, without limitation: (i) biotin; (ii) an antibody; (iii) an enzyme; (iv) lipopolysaccharide; (v) apotransferrin; (vi) ferrotransferrin; (vii) insulin; (viii) cytokines (growth factors, interleukins or colony-stimulating factors); (ix) gp120; (x) $\beta$-actin; (xi) LFA-1; (xii) Mac-1; (xiii) glycophorin; (xiv) laminin; (xv) collagen; (xvi) fibronectin; (xvii) vitronectin; (xviii) integrins $\alpha_v\beta_1$ and $\alpha_v\beta_3$; (xix) integrins $\alpha_3\beta_1$, $\alpha_4\beta_1$, $\alpha_4\beta_7$, $\alpha_5\beta_1$, $\alpha_v\beta_1$, $\alpha_{IIb}\beta_3$, $\alpha_v\beta_3$ and $\alpha_v\beta_6$; (xx) integrins $\alpha_1\beta_1$, $\alpha_2\beta_1$, $\alpha_3\beta_1$ and $\alpha_v\beta_3$; (xxi) integrins $\alpha_1\beta_1$, $\alpha_2\beta_1$, $\alpha_3\beta_1$, $\alpha_6\beta_1$, $\alpha_7\beta_1$ and $\alpha_6\beta_5$; (xxii) ankyrin; (xxiii) C3bi, fibrinogen or Factor X; (xxiv) ICAM-1 or ICAM-2; (xxv) spectrin or fodrin; (xxvi) CD4; (xxvii) a cytokine (e.g., growth factor, interleukin or colony-stimulating factor) receptor; (xxviii) an insulin receptor; (xxix) a transferrin receptor; (xxx) $Fe^{+++}$; (xxxi) polymyxin B or endotoxin-neutralizing protein (ENP); (xxxii) an enzyme-specific substrate; (xxxiii) protein A, protein G, a cell-surface Fc receptor or an antibody-specific antigen; (xxxiv) avidin and streptavidin; and combinations thereof. A particularly preferred hapten for use in the methods of the invention is biotin. The haptenylated nucleic acid molecules, in which one or more hapten molecules are attached (preferably covalently) to one or more nucleotides of the nucleic acid molecule, may be produced using conventional organic synthesis methods that will be familiar to one of ordinary skill in the art. For example, the nucleic acid molecule may be biotinylated at the 5' terminus by first producing 5' amino ($NH_2$) groups followed by Cab-NHS ester addition (Langer, P. R., et al., *Proc. Natl. Acad. Sci. USA* 78:6633 (1981)). In a particularly preferred aspect of the invention, a haptenylated nucleic acid molecule, which may be an RNA molecule or a DNA molecules, comprising one or more, two or more, three or more or four or more hapten molecules, most preferably biotin molecules, is prepared.

Once the haptenylated nucleic acid molecules that are complementary to the nucleic acid molecules of the library have been produced, they are used to normalize the nucleic acid library by hybridization. Specifically, the nucleic acid library to be normalized is preferably incubated with a molar excess of the population of haptenylated nucleic acid molecules (e.g. greater than or equal to 10 fold or preferably greater than or equal to 20 fold molar excess), prepared as described above, under conditions favoring the more rapid hybridization of the haptenylated nucleic acid molecules to the more highly abundant nucleic acid molecules and less rapid hybrid to the less abundant nucleic acid molecules present in the library. Such conditions favoring hybridization may comprise, for example, incubating the library to be normalized with the haptenylated nucleic acid molecules at a range of COTs. COT is the product of the starting concentration of nucleic acid (moles of nucleotide per liter, Co) and time (seconds, t). The COT is obtained by converting the concentration of reacting nucleotides and time of hybridization into standard units (mol·sec·L$^{-1}$ or M·sec). As described in detail in the Examples below, particularly preferred COTs for use in the present methods include, but are not limited to: a COT equal to or greater than 25; a COT equal to or greater than 50; a COT equal to or greater than 100; a COT equal to or greater than 200; a COT equal to or greater than 250; a COT equal to or greater than 500; a COT equal to or greater than 1000; and a COT of less than about 10,000. Alternatively, hybridization conditions consisting of a range of COTs may be used, including a COT from about 10 to about 10,000; a COT from about 25 to about 10,000; a COT from about 50 to about 10,000; a COT from about 100 to about 10,000; a COT from about 200 to about 10,000; a COT from about 250 to about 10,000; and a COT from about 500 to about 10,000. Other hybridization conditions suitable for use with the present methods will be apparent to one of ordinary skill and may be determined with only routine experimentation.

Under these conditions, the haptenylated nucleic acid molecules hybridize more rapidly to the more highly abundant nucleic acid molecules present in the library and less rapidly to the less abundant members. The hybridization complexes formed between the library and the haptenylated nucleic acid molecules may then be removed by a variety of methods, resulting in the reduction in copy number of the highly abundant nucleic acid molecules in the library and thus producing a normalized nucleic acid library.

According to the invention, removal of the complexes is accomplished by ligand-hapten interactions using a ligand which binds specifically to the hapten that is bound to the haptenylated nucleic acid molecules. In a preferred such method, the ligand may be bound, preferably covalently, to a solid support such as nitrocellulose, diazocellulose, glass, polystyrene (including microtitre plates), polyvinylchloride, polypropylene, polyethylene, dextran, Sepharose, agar, starch, nylon, or beads, which may be latex beads, magnetic beads, paramagnetic beads, superparamagnetic beads or glass beads. Particularly preferred solid supports are magnetic beads, paramagnetic beads and superparamagnetic beads, which are commercially available, for example from Life Technologies, Inc. (Rockville, Md.), Dynal A. S. (Oslo, Norway), or from Sigma (St. Louis, Mo.).

Coupled to these solid supports may be any ligand capable of binding the hapten used to haptenylate the nucleic acid molecules. Examples of suitable ligands for use in the present methods (which correspond in order to the hapten molecules listed above) include without limitation: (i) avidin and streptavidin; (ii) protein A, protein G, a cell-surface Fc receptor or an antibody-specific antigen; (iii) an enzyme-specific substrate; (iv) polymyxin B or endotoxin-neutralizing protein (ENP); (v) Fe$^{+++}$; (vi) a transferrin receptor; (vii) an insulin receptor; (viii) a cytokine (e.g., growth factor, interleukin or colony-stimulating factor) receptor; (ix) CD4; (x) spectrin or fodrin; (xi) ICAM-1 or ICAM-2; (xii) C3bi, fibrinogen or Factor X; (xiii) ankyrin; (xiv) integrins $\alpha_1\beta_1$, $\alpha_2\beta_1$, $\alpha_3\beta_1$, $\alpha_6\beta_1$, $\alpha_7\beta_1$ and $\alpha_6\beta_5$; (xv) integrins $\alpha_1\beta_1$, $\alpha_2\beta_1$, $\alpha_3\beta_1$ and $\alpha_v\beta_3$; (xvi) integrins $\alpha_3\beta_1$, $\alpha_4\beta_1$, $\alpha_4\beta_7$, $\alpha_5\beta_1$, $\alpha_v\beta_1$, $\alpha_{IIb}\beta_3$, $\alpha_v\beta_3$ and $\alpha_v\beta_6$; (xvii) integrins $\alpha_v\beta_1$ and $\alpha_v\beta_3$; (xviii) vitronectin; (xix) fibronectin; (xx) collagen; (xxi) laminin; (xxii) glycophrin; (xxiii) Mac-1; (xxiv) LFA-1; (xxv)β-actin; (xxvi) gp120; (xxvii) cytokines (growth factors, interleukins or colony-stimulating factors); (xxviii) insulin; (xxix) ferrotransferrin; (xxx) apotransferrin; (xxxi) lipopolysaccharide; (xxxii) an enzyme; (xxxiii) an antibody;(xxxiv) biotin; and combinations thereof. Preferred ligands include avidin and streptavidin. Of course, the choice of ligand will depend upon the choice of hapten used in the production of the haptenylated nucleic acid molecule; appropriate ligands for use in the methods of the invention will thus be apparent to one of ordinary skill in the art. Linkage of the ligand molecule(s) to the solid support can be accomplished by any method of ligand coupling such as covalent, hydrophobic or ionic coupling (including coating) that will be familiar to one of ordinary skill in the art. For example, in a preferred aspect of the invention where the haptenylated nucleic acid molecules comprise biotin, a biotin-binding ligand such as avidin or streptavidin may be linked to the solid support. In a particularly preferred such aspect, the solid support used is avidin- or streptavidin-coupled magnetic, paramagnetic or superparamagnetic beads.

Typically, conditions favoring ligand-hapten interactions include incubation in a buffered salt solution, preferably a TRIS-, phosphate-HEPES- or carbonate-buffered sodium chloride solution, more preferably a TRIS-buffered sodium chloride solution, still more preferably a solution comprising about 10–100 mM TRIS-HCl and about 300–2000 mM NaCl, and most preferably a solution comprising about 10 mM TRIS-HCl and about 1 M NaCl, at a pH of about 6–9, more preferably a pH of about 7–8, still more preferably a pH of about 7.2–7.6, and most preferably a pH of about 7.5. Incubation is preferably conducted at 0° C. to about 25° C., and most preferably at about 25° C., for about 30–120 minutes, preferably about 45–90 minutes, and most preferably about 60 minutes, to allow the binding of the haptenylated nucleic acid molecules (and thus the complementary library nucleic acid molecules to which they are hybridized) to the ligand-coupled solid support.

Once the haptenylated complexes have been bound to the solid phase support, the normalized nucleic acid library, comprising nucleic acid molecules of a lower range of abundances than the input library, may be collected from the supernatants or eluates (i.e., the unbound materials in solution). For example, in a preferred aspect in which biotinylated nucleic acid molecules are bound to avidin or streptavidin; or a avidin- or streptavidin-coupled solid phase, the nucleic acid molecules comprising the normalized nucleic acid library, such as a normalized cDNA library, may be obtained by gently aspirating and collecting the supernatants. In a particularly preferred aspect in which avidin- or streptavidin-coupled magnetic, paramagnetic or superparamagnetic beads are used as the solid support, the biotinylated nucleic acid-containing beads may be segregated from the supernatants using a magnet (such as a Magna-Sep Magnetic Particle Separator; Life Technologies, Inc.) and the supernatants may be withdrawn using a pipette. Removal of the haptenylated complexes is preferably accomplished by extraction with an organic solvent (e.g. phenol, chloroform etc.). The above described approaches result in the production of a normalized nucleic acid library, which may be single-stranded or double-stranded and which may be used immediately, stored until use, or processed and further purified in accordance with the invention or by techniques that are well-known in the literature (see, e.g., Gubler, U., and Hoffman, B. J., *Gene* 25:263–269 (1983); Krug, M. S., and Berger, S. L., *Meth. Enzymol.* 152:316–325 (1987); Sambrook, J., et al., *Molecular Cloning: A Laboratory Manual,* 2nd ed., Cold Spring Harbor, N.Y.: Cold Spring Harbor Laboratory Press, pp. 8.60–8.63 (1987)), and others that will be familiar to one of ordinary skill in the art.

Background Reduction or Elimination

The invention also provides methods for the production of a selected normalized nucleic acid library with very low non-recombinant and rearranged clone background. As used herein, a selected normalized library is a library in which one or more specific nucleic acid molecules or sets of nucleic acid molecules have been enriched in the normalized library and other nucleic acid molecules of less interest have been removed by one or several approaches described herein. Thus, the invention further relates to removal of contaminating or background nucleic acid molecules from the normalized library. In accordance with the invention, such removal or elimination of contaminating nucleic acids may be performed prior to or after normalization. Typical contaminating nucleic acid molecules in a library are vector molecules which do not contain nucleic acid molecules of the library (where the vector failed to receive an insert or the vector lost the insert by deletion during propagation of the source library).

In accordance with the invention, target-specific probes (e.g. oligodA-NotI) may be used in a number of methods to reduce or remove contaminated nucleic acids from the library of interest. Such probes are target-specific in that they recognize and hybridize to molecules of the library molecules but not to contaminating nucleic acid sequences (such as vectors without library inserts. One such means involves using one or more haptenylated target-specific probes to capture or isolate the library of interest. In such methods, the normalized library is preferably single-stranded (or, if double-stranded, is made single-stranded by methods described herein). By hybridizing the haptenylated probes to the normalized library, the hybridized normalized library may be selected away from contaminating nucleic acid using, for example, hapten/ligand interactions or extraction. The resulting single-stranded selected normalized library may then be made double stranded by incubating the library with one or more polypeptides having polymerase activity under conditions sufficient to synthesize double-stranded selected normalized library.

Alternatively, the normalized library is hybridized to a target-specific, haptenylated primer and the molecules may then be made double-stranded by incubating them with one or more polypeptides having polymerase activity under conditions sufficient to synthesize double-stranded normalized library. In making such molecules double-stranded, one or more nuclease-resistant nucleotides may be used. The double-stranded molecules may then be selected away from the contaminating nucleic acid molecules using, for example, hapten/ligand interactions or extraction.

In both cases, the resulting double stranded selected normalized library of the invention may then be transformed into one or more host cells in a further selection step. In accordance with the invention, single stranded molecules are transformed at a very low frequency while double stranded molecules are transformed at a very high frequency. Thus, transformation allows for an additional selection step in which single stranded contaminating molecules are eliminated or removed. For example, when a target specific probe or primer is used in the double stranded synthesis step, non-specific nucleic acids are not primed and thus are not made double stranded and will not be present in the selected normalized library.

In another aspect of the invention, single-stranded selected normalized library selected with the haptenylated probes are made double-stranded with primers (preferably target specific primers) and one or more nucleotides which confer nuclease resistance to the synthesized double-stranded molecule. Digestion with such a nuclease allows removal of single-stranded molecules which have not been made double stranded by the primers. Such double-stranded molecules may then be transformed into one or more host cells as an additional selection step.

In yet another aspect, the selected normalized library may be prepared by incubating the single-stranded normalized library with one or more target-specific primers which are not haptenylated in combination with one or more nucleotides which confer nuclease resistance. Digestion of the mixture provides for the selection of the desired nucleic acid molecules and as a additional selection step, the resulting double-stranded molecules may be transformed into one or more host cells.

In accordance with the invention, single stranded molecules may be made from double stranded by treating double-stranded molecules under conditions sufficient to render them single-stranded. Such conditions may comprise, for example, degradation of one strand of the double-stranded nucleic acid molecules in the library, such as by using an endonuclease, an exonuclease, and the like, and preferably by using gene II protein and exonuclease III (available from Life Technologies, Inc., Rockville, Md.). Alternatively, such conditions may comprise denaturing the double-stranded molecules with heat, ionic conditions, pH (e.g. base) and the like.

Nucleotides which confer nuclease resistance used in accordance with the invention are preferably nucleotide analogs. Such nucleotide analogs include but are not limited to methylated nucleotides such as 5-methyldeoxycytosine, 3-methyldeoxyadenosine, 7-methylguanine and the like. Other nucleotide analogs that inhibit or block exonucleases or restriction endonucleases (nucleases) will be recognized by those skilled in the art. Combinations of nucleotide analogs and suitable enzymes that may be used according to the invention also known in the art (see Life Technologies 1997–1998 Catalog and Reference Guide, Chapter 6).

Kits

The present invention also provides kits for use in production and isolation of normalized and selected normalized libraries. Kits according to this aspect of the invention comprise a carrier means, such as a box, carton, tube or the like, having in close confinement therein one or more containers, such as vials, tubes, ampules, bottles and the like. The kit of the invention may comprise the driver for normalizing a library or the components needed to make the driver used to normalize a library (for example, one or more polymerases, one or more adapters comprising promoters, one or more vectors comprising promoters, one or more haptenylated nucleotides and/or one or more haptenylated primers or probes). Such kits may comprise one or more target specific probes or primers (which are haptenylated or not). In additional aspects, the kits of the invention may comprise one or more nucleotides (e.g., nucleotides which confer nuclease resistance and/or one or more endonucleases, exonucleases or restriction enzymes, such as gene II protein or exonuclease III or HhaI, used for digestion of the nucleic acid molecules.

Additional kits provided by the invention comprise one or more containers containing one or more of the above-described normalized nucleic acid libraries or selected normalized nucleic acid libraries of the invention. The libraries in these kits of the invention may be single-stranded or double-stranded, and are preferably cDNA libraries.

The kits encompassed by this aspect of the present invention may further comprise one or more additional reagents (e.g., suitable buffers) and compounds necessary for using the normalized libraries and selected normalized libraries of the invention.

Uses

The present invention can be used in a variety of applications requiring rapid production and isolation of normalized and selected normalized nucleic acid libraries, particularly cDNA libraries. The primary use for such libraries is for gene discovery and for preparing gene databases. Libraries prepared by the methods of the invention may be used as sources of template nucleic acid molecules for amplification reactions (such as via PCR), to rapidly identify and/or clone low copy number nucleic acid molecules, and to produce polypeptides by genetic engineering techniques.

The invention thus is also directed to methods for the amplification of a nucleic acid molecule, and to nucleic acid molecules amplified by to these methods. According to this aspect of the invention, a nucleic acid molecule may be amplified (i.e., additional copies of the nucleic acid molecule prepared) by amplifying a nucleic acid molecule (e.g., a cDNA molecule) contained in a normalized library or selected normalized library of the invention according to any amplification method that is known in the art. Particularly preferred amplification methods according to this aspect of the invention include PCR (U.S. Pat. Nos. 4,683,195 and 4,683,202), Strand Displacement Amplification (SDA; U.S. Pat. No. 5,455,166; EP 0 684 315), and Nucleic Acid Sequence-Based Amplification (NASBA; U.S. Pat. No. 5,409,818; EP 0 329 822); the disclosures of each of the foregoing U.S. patent documents are incorporated by reference herein in their entireties. Most preferred are those methods comprising one or more PCR amplifications.

The invention is also directed to methods that may be used to prepare vectors which comprise the normalized or selected normalized libraries of the present invention, to host cells which comprise these vectors, to methods for the production of a recombinant polypeptide using these vectors and host cells, and to recombinant polypeptides produced using these methods. According to this aspect of the invention, a recombinant polypeptide may be produced by culturing any of the above recombinant host cells under conditions favoring production of a polypeptide therefrom, and isolation of the polypeptide. Methods for culturing recombinant host cells, and for production and isolation of polypeptides therefrom, are well-known to one of ordinary skill in the art.

Vectors are produced according to the invention by inserting, using methods that are well-known in the art, one or more of the nucleic acid molecules of interest into a vector. The vector used in this aspect of the invention may be, for example, a plasmid, a cosmid or a phage. Preferred are vectors comprising cis-acting control regions to the nucleic acid encoding the polypeptide of interest. Appropriate trans-acting factors may be supplied by the host, supplied by a complementing vector or supplied by the vector itself upon introduction into the host.

In certain preferred embodiments, the vectors are expression vectors that provide for specific expression of the nucleic acid molecules contained in the normalized libraries or selected normalized libraries of the invention, which vectors may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids or bacteriophages, and vectors derived from combinations thereof, such as cosmids and phagemids, and will preferably include at least one selectable marker such as a tetracycline or ampicillin resistance gene for culturing in a bacterial host cell. Prior to insertion into such an expression vector, the nucleic acid molecules contained in the libraries of the invention may be operatively linked to an appropriate promoter, such as the phage lambda PL promoter, the *E. coli* lac, trp and tac promoters. Other suitable promoters will be known to the skilled artisan. Among vectors preferred for use in the present invention include pQE70, pQE60 and pQE-9, available from Qiagen; pBS vectors, Phagescript vectors, Bluescript vectors, pNH8A, pNH16a, pNH18A, pNH46A, available from Stratagene; pcDNA3 available from Invitrogen; pGEX, pTrxfus, pTrc99a, pET-5, pET-9, pKK223-3, pKK233-3, pDR540, pRIT5 available from Pharmacia; and pSPORT1, pSPORT2, pCMVSPORT 2.0 and pSV.SPORT1, available from Life Technologies, Inc. Other suitable vectors will be readily apparent to the skilled artisan.

Representative host cells that may be used according to the invention include, but are not limited to, bacterial cells, yeast cells, plant cells and animal cells. Preferred bacterial host cells include Escherichia spp. cells (particularly *E. coli* cells and most particularly *E coli* strains DH10B and Stb12), Bacillus spp. cells (particularly *B. subtilis* and *B. megaterium* cells), Streptomyces spp. cells, Erwinia spp. cells, Klebsiella spp. cells and Salmonella spp. cells (particularly *S. typhimurium* cells). Preferred animal host cells include insect cells (most particularly *Spodoptera frugiperda* Sf9 and Sf21 cells and Trichoplusa High-Five cells) and mammalian cells (most particularly CHO, COS, VERO, BHK and human cells). These and other suitable host cells are available commercially, for example from Life Technologies, Inc. (Rockville, Md.), American Type Culture Collection (Rockville, Md.) and Invitrogen (San Diego, Calif.).

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Figure 2:
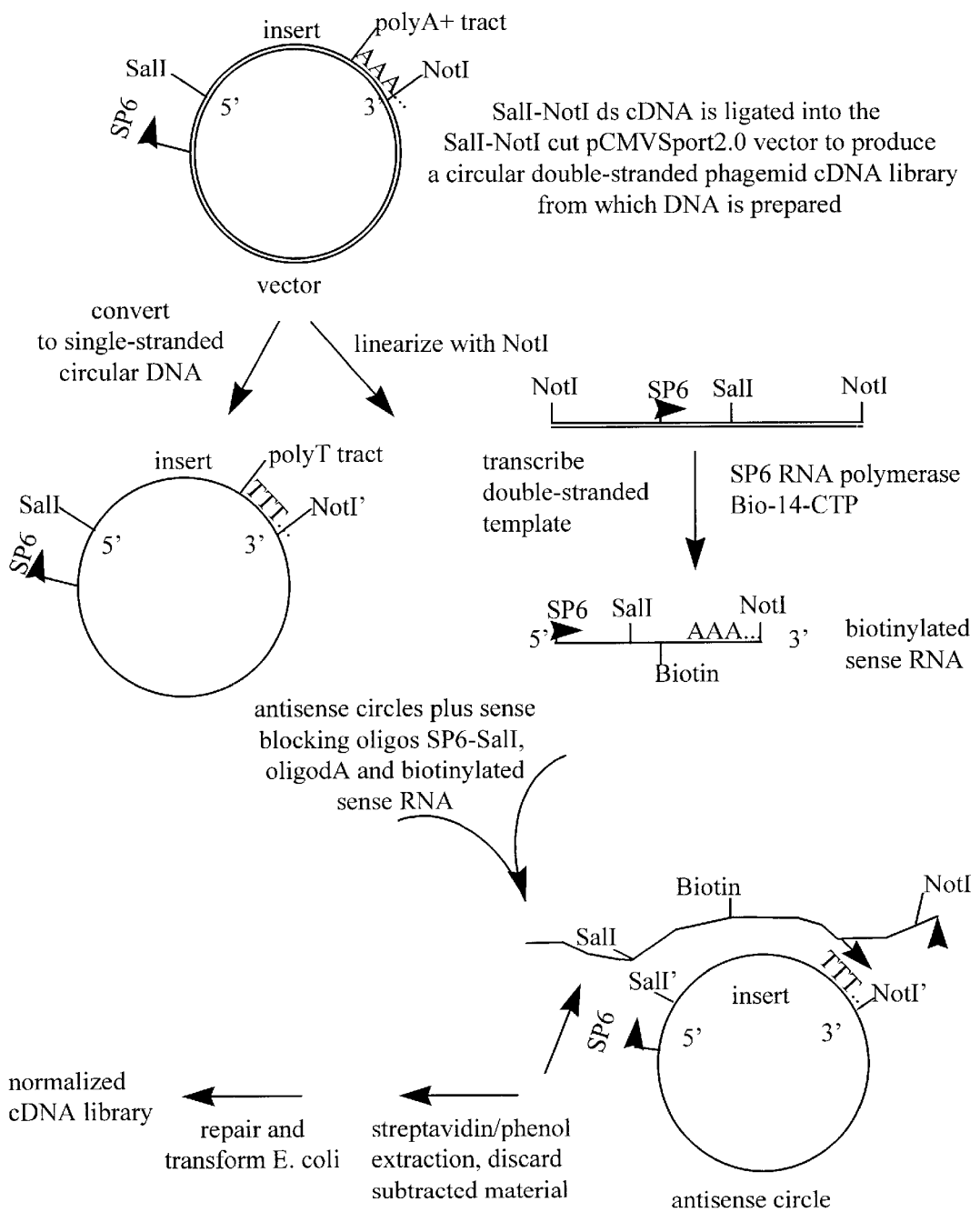
FIG. 2 is a schematic diagram of the production of normalized phagemid libraries using subtractive hybridization with a biotinylated total library RNA driver referred to synonymously as haptenylated nucleic acid molecules.

Production of Normalized cDNA Libraries from Directionally-cloned cDNA Libraries The process of constructing a normalized cDNA library in the pCMVSPORT 2.0 vector is described in this example (FIGS. 1 and 2). It consists of i) isolating phagemid DNA from a directionally cloned cDNA library, ii) converting the double-stranded (ds) circular cDNA library DNA into a) a linear ds template for RNA polymerase production of biotinylated RNA driver and b) single-stranded (ss) circular DNA using GeneII and Exonuclease III, iii) combining the driver and ss circular library DNA with two blocking oligonucleotides in a subtraction hybridization, iv) repairing the non-subtracted ss circular DNA and v) transforming it into *E. coli* cells thus producing a primary normalized cDNA library.

Production of circular ss DNA from circular ds cDNA library DNA is done in the following way. Digest 10 µg of circular ds cDNA in 1×GeneII buffer 20 mM Tris.HCl (pH=8), 80 mM NaCl, 25 mM MgCl$_2$, 2 mM β-mercaptoethanol. 5% glycerol, 5 mg/ml BSA with 8 µl GeneII at 30° C. for 40 min in a final volume of 200 µl. Terminate the reaction by incubation at 65° C. for 5 min. Add 12 µl of exonuclease III, and incubate at 37° C. for 30 min. Add 8 µl (10 U/µl) of NotI and incubate the mixture for 1 h at 37° C. Add 2 µl of exonuclease III, and continue to incubate for 1 hour at 37° C. Extract twice with phenol/chloroform/isoamyl alcohol (25:24:1) and ethanol precipitate. Resuspend the circular ss cDNA in 10 µl of RNASE-free TE. Fetal Brain cDNA library (Life Technologies, Inc., Rockville, Md.) was made single stranded by this procedure.

Production of linearized ds cDNA from circular ds cDNA is as follows. Digest 50 µl of circular ds cDNA with 200 units of NotI (LTI) in 300 µl of 1× reaction buffer [5 mM Tris.HCl, pH 8.0; 1 mM MgCl$_2$; 10 mM NaCl] for 3 hours at 37° C. Add 100 units of NotI, and incubate an additional 3 hours at 37° C. Extract twice with phenol/chloroform/isoamyl alcohol (25:24:1 v/v) and ethanol precipitate. Resuspend the linearized ds cDNA in 30 µl of RNASE-free TE buffer. Human Fetal Brain cDNA library (Life Technologies, Inc., Rockville, Md.) was linearized in this manner.

Production of biotinylated RNA driver from circular ds cDNA library DNA is done in the following way. Prepare a mixture of the following components: 1.214 ml DEPC-treated water, 400 µl 5× transcription buffer [200 mM Tris-HCl (pH 7.9), 30 mM MgCl$_2$, 10 mM spermidine-(HCl)$_3$], 200 µl rNTP mix (10 µM each ATP, GTP and UTP, 5 µM CTP, 20 µM biotin-14-CTP), 16 µl (20 µg) linearized ds from a Human Fetal Brain cDNA library (see above), 100 µl 0.1 M DTT, and 70 µl SP6 RNA polymerase (350 units/µl). The Human Fetal Brain cDNA library (Life Technologies, Inc., Rockville, Md.) was constructed in pCMV.SPORT vector which contains a CMV promoter, an SP6 and T7 polymerase promoter flanking the multiple cloning site (MSC) for RNA driver synthesis. Mix and incubate at 37° C. for 13 hours. Add 1 ml of 7.5 M ammonium acetate and 8 ml of ethanol. Cool on dry ice for 30 min, microcentrifuge for 25 min at 4° C. and resuspend the pellet in 1 ml of TE. Heat the solution at 65° C. and reprecipitate again. Wash the pellet in 70% ethanol, dry and resuspend in 1.92 ml water, 40 µl of 1M Tris-HCl, [pH 7.5], heat at 65° C. for resuspension. Add 20 µl 1M MgCl$_2$, 20 µl DNaseI (2,660 units) to the resuspended RNA and incubate at 37° C. for 1 hr. Transfer the treated RNA to a fresh tube and add 40 µl of 0.5 M EDTA, incubate at 65° C. for 10 min. and precipitate it with 1 ml of 7.5 M ammonium acetate plus 8 ml ethanol. Resuspend the pellet in 300 µl of TE, heat at 65° C. to aid resuspension and load onto a 1 cm×18 cm column (Sephadex G-50) and collect the first peak detected by UV absorbance at 260 nm. Precipitate the collected material (~4 ml) with 2 ml of 7.5 M ammonium acetate and 16 ml ethanol. Resuspend the pellet in 120 µl TE, wash the tube with 20 µl TE and pool the 2 samples. This procedure provides haptenylated driver of the Human Fetal Brain cDNA library for use in normalization of the Human Fetal Brain cDNA library.

Subtractive hybridization is carried out using the following procedure. Denature a mixture of the following components at 80° C. for 1 min: 1 µg circular ss cDNA library (see above), 0.5 µg of the oligodA oligonucleotide 5' (A)$_{40}$ 3' (oligo dA), 3 µg of SP6 promoter-SalI sense oligonucleotide 5'GAA GGT ACG CCT GCA GGT ACC GGT CCG GAA TTC CCG GGT CGA CCC ACG 3' (SEQ ID NO:1) (SP6-SalI), 0.25 M NaCl in 22 µl of 1×hybridization buffer [50 mM HEPES (pH 7.5), 1 mM EDTA and 0.1% SDS]. After denaturation, incubate the mixture at room temperature for 30 min.

For the COT=500, library denature 85 µg of the biotinylated RNA driver (see above) in 22 µl of 1×hybridization buffer at 90° C. for 2 min, chill on ice for 1 min, and add 1 µl of 5 M NaCl. Transfer the prehybridized circular ss DNA to the biotinylated RNA driver and incubate at 42° C. for 24 hr. For the COT=5 library, 10.5 µg of RNA driver is hybridized for 2 hrs; for the COT=50 library, 41 µg of RNA driver is hybridized for 5 hrs; for the COT=0 library, no RNA driver is added and the mixture is incubated for 24 hrs.

Following the incubation, transfer the mixture to a fresh tube, add 25 µg of streptavidin and incubate at room temperature for 5 min. Extract the solution with an equal volume of PCIA (phenol/chloroform/isoamyl alcohol, 25.24:1). Back-extract the organic phase with 15 µl of TE containing 1 M NaCl and pool the aqueous extractions. Repeat the streptavidin binding and PCIA extraction twice more. Precipitate the aqueous phase with 0.3 M sodium acetate and ethanol. Resuspend the pellet in 15 µl TE and dialyze against TE (10 mM:0.5 mM) for 30 min. Transfer the DNA to a fresh tube and measure the volume. This resulting cDNA is a single-stranded normalized cDNA library.

Analysis of clones following subtraction is done in the following way. When the circular ss cDNA that remains following subtraction is converted into ds cDNA using an oligodA-NotI primer, dNTPs, a repair polymerase and is transformed into *E. coli* cells, a large fraction of the transformants contain plasmids that do not contain inserts (Table 1).

TABLE 1

Percent Recombinant cDNA Clones and Average Insert Size Following Total Human Fetal Brain cDNA Library Subtraction.

| Human Fetal Brain cDNA Library | % recombinants (24 independent clones) | Average insert size (kb) |
|---|---|---|
| Cot = 0 | 92 | 1.3 |
| Cot = 5 | 79 | 1.2 |
| Cot = 50 | 67 | 1.4 |
| Cot = 500 | 45 | 1.1 |

After analysis of the clones that do not contain inserts, it was determined that they were present in the original library at a frequency of less than 1%, but were enriched following subtraction since they have no corresponding driver molecule to subtract them (FIG. 2). Two approaches were developed to remove this form of background and are described in Examples 2 and 3.

Example 2

Figure 3:
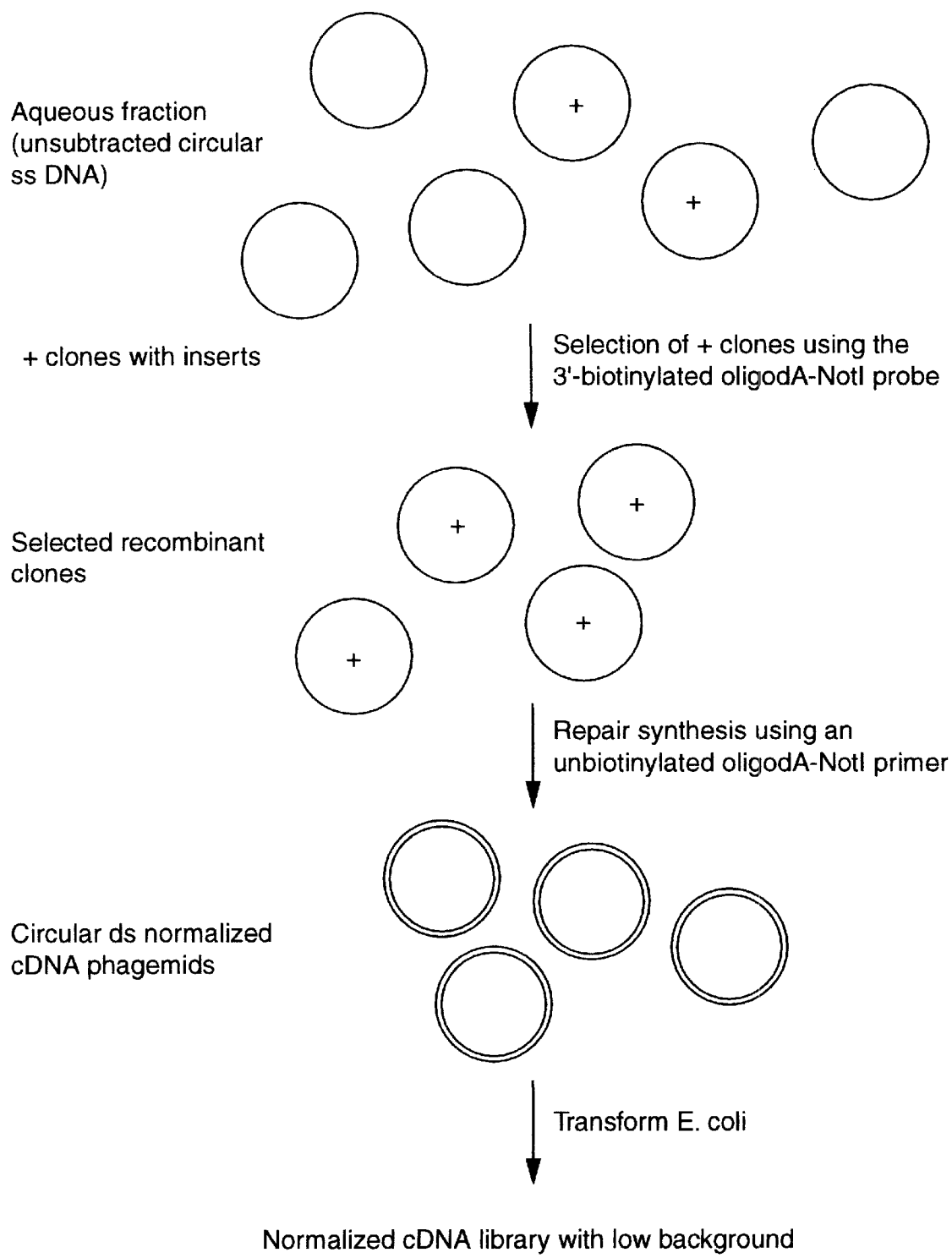
FIG. 3 is a diagram showing how 3' biotinylated target specific probes can be used to produce low-background normalized phagemid libraries also referred to herein as selected normalized libraries.
Figure 4:
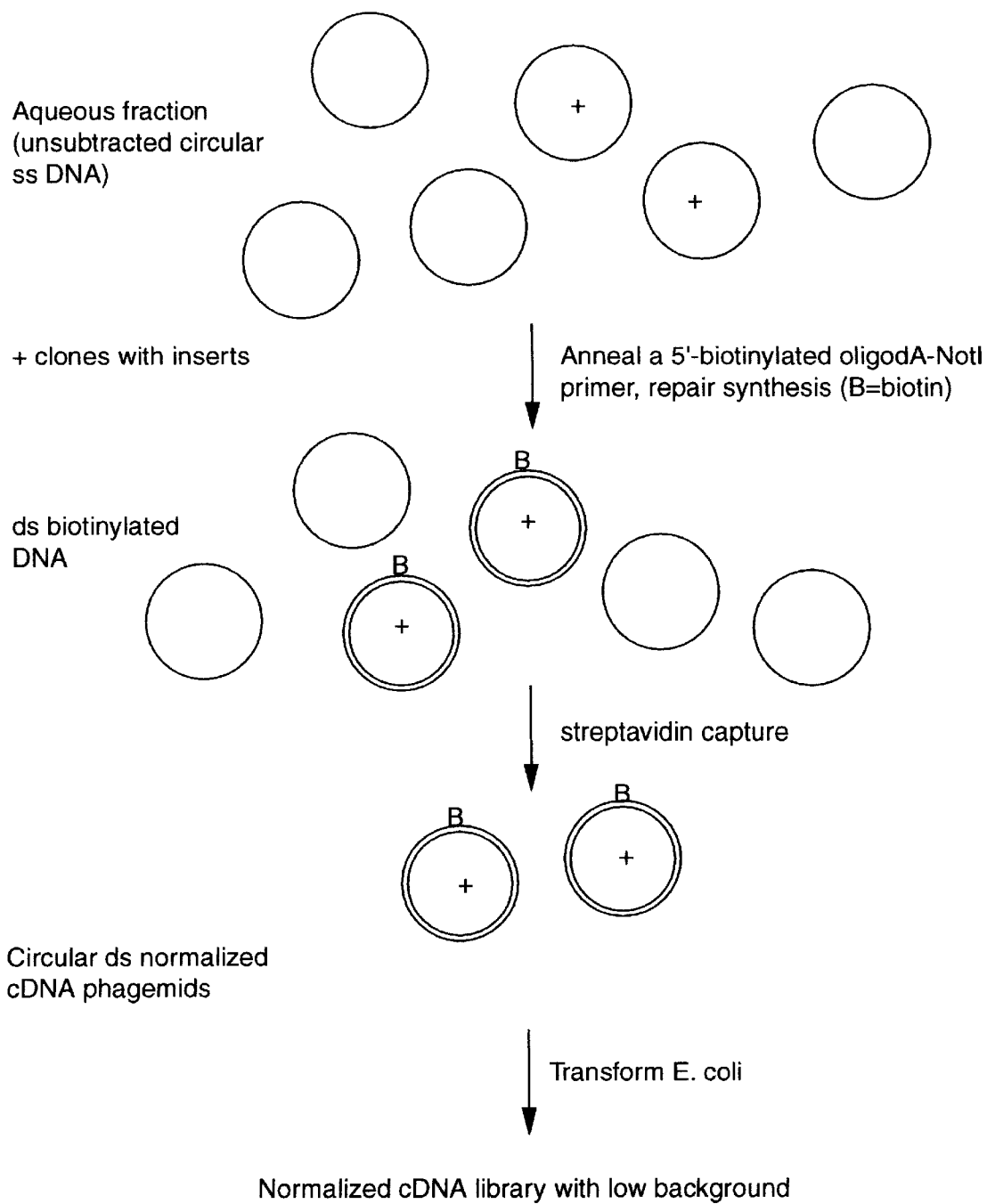
FIG. 4 is a diagram showing how a 5' biotinylated target specific probe can be used to reduce background in normalized phagemid libraries also referred to herein as selected normalized libraries.

Removal of Background from a Normalized cDNA Library Using Selection with a Target Specific Biotinylated OligodA-NotI Probe As a result of the subtraction process described in Example 1, there is a trend of increased background that depends directly on the COT of the subtraction step (Table 1). Since a total library driver is used, clones that do not contain a counterpart in the driver will be enriched. This was observed in the process described in Example 1 (FIG. 2). To address this issue, two methods were developed and a third is described to virtually eliminate the background. In the first case, described in this example, selection of recombinant clones using an oligodA-NotI biotinylated probe was used (FIG. 3) as follows.

Following subtraction, repair and transformation, 45% of the clones derived from the COT=500 protocol were recombinant (Table 1), however by using probe selection with a biotinylated oligodA-NotI primer (5'(A)$_{15}$GGG CGG CCG C 3') (SEQ ID NO:2), the recombinant clones were selected away from the non-recombinants permitting construction of a normalized cDNA library with no significant change in average insert size and the virtual elimination of non-recombinant clones (Table 2).

TABLE 2

Percentage of Recombinant cDNA Clones and Average Insert Size Following Total Human Fetal Brain cDNA Library Subtraction and GENETRAPPER ™ Selection with a Biotinylated OligodA-NotI Probe

| Human Fetal Brain cDNA Library | % recombinants (96 independent clones) | Average insert size (kb) |
|---|---|---|
| Cot = 500 | 99 | 1.25 |

Figure 6:
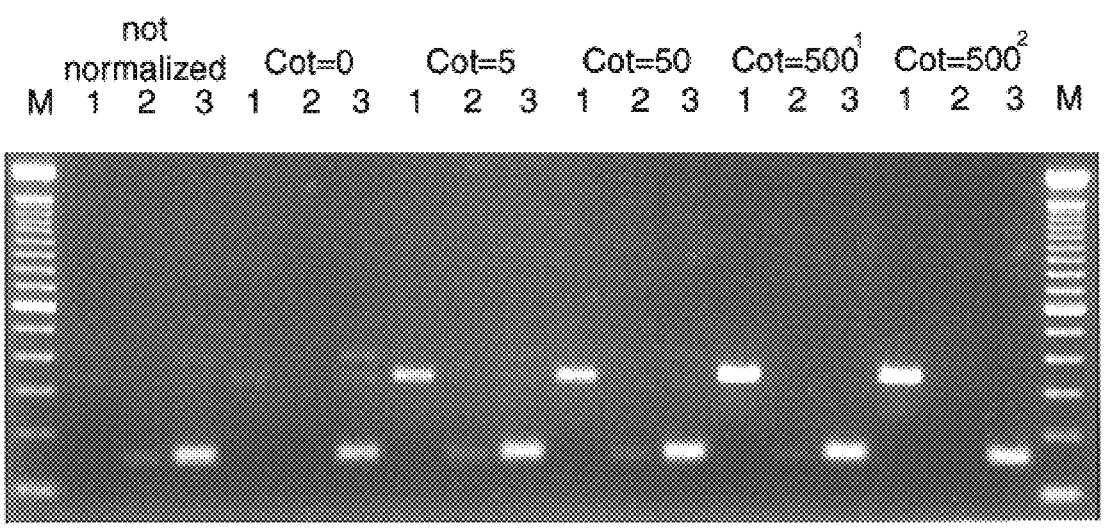
FIG. 6 is a photograph of an ethidium bromide-stained gel of the enrichment of various TGFβ cDNAs, that are present at considerably different abundances in an unnormalized cDNA library, at different COTs of subtraction in a normalized human fetal brain cDNA library for which two different background elimination methods have been applied.
Figure 7:
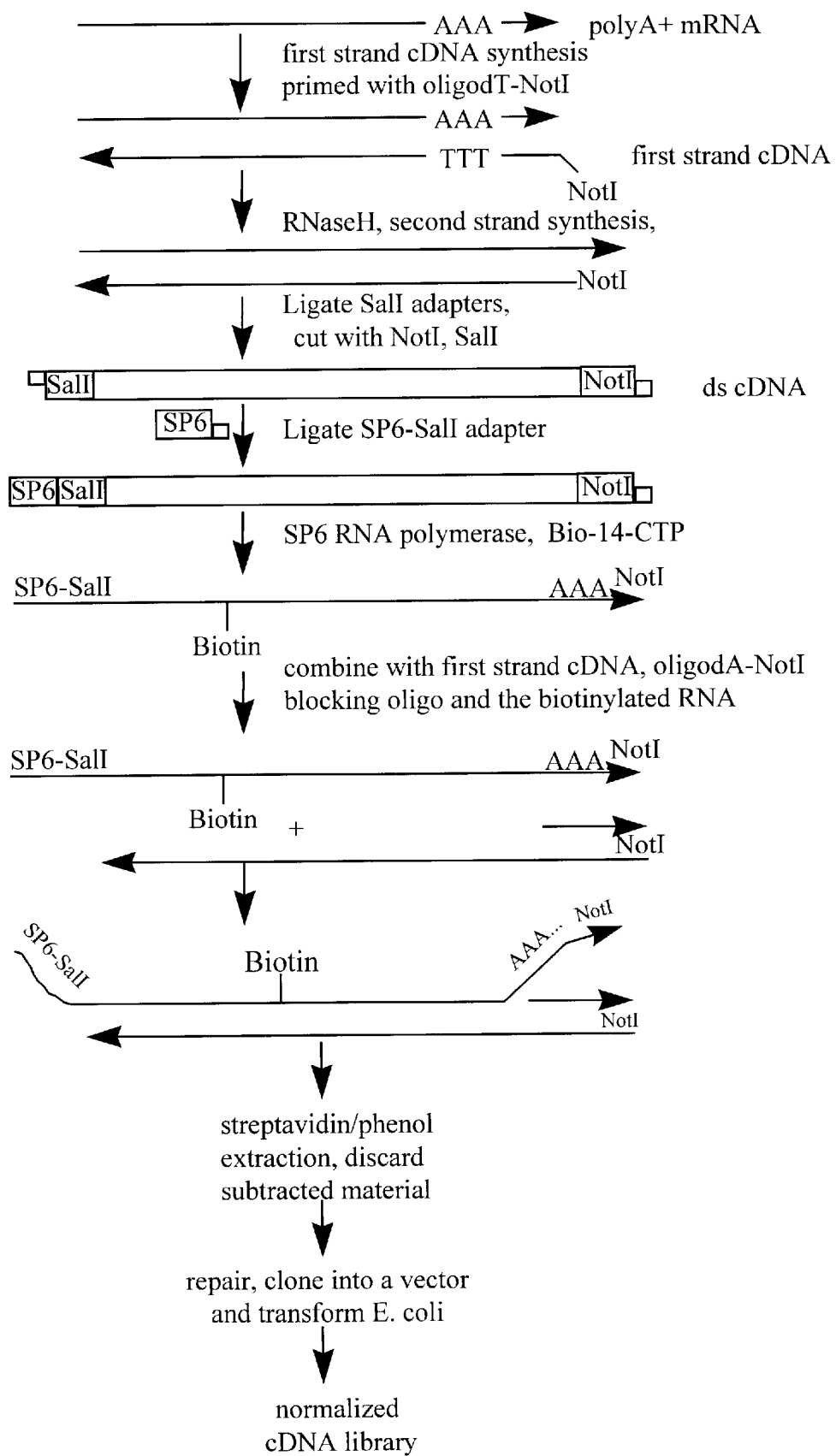
FIG. 7 is a schematic representation of the normalization of a library using adaptors comprising promoters. Following normalization, the library may be cloned into a vector. In this method, removal of contaminating vector sequences may be unnecessary, since the selection of background sequences can be undertaken prior to cloning.

More than 98% of the clones picked at random contain inserts that are on average as large as the non-normalized cDNA library from which they were derived. In addition, PCR analysis of rare and abundant TGF-β amplicons indicates that substantial normalization has been accomplished (FIG. 6). Note that although the TGF-β1 PCR product is undetectable in the non-normalized and low COT libraries, it is detected in the higher Cot libraries.

The normalized circular ss cDNA from Example 1 was heated at 70° C. for 1 min and chilled on ice for 1 min. 200 ng of the biotinylated oligodA-NotI primer (see above), was hybridized at 37° C. for 1 hr. The hybridization mixture was incubated with 80 µg of streptavidin magnetic beads. The beads were marked three times with 100 µl of wash buffer (10 mM Tris.HCl [pH 7.5], 1 mM EDTA). The beads were resuspended in 20 µl 1×elution buffer 10 mM glycine and the eluate was saved. The elution step was repeated with 15 µl of 1×elution buffer and the eluates were pooled. This protocol was repeated three times and the eluates. The captured single stranded cDNA was repaired as follows: Make a repair mix by combining 4 µl of 10×repair buffer [100 mM Tris-HCl (pH 8.8 at 25° C.), 15 mM MgCl$_2$, 500 mM KCl, 1% Triton X-100], 1 µl 10 mM dNTP, 1 µl of repair enzyme Dynazyme (2 m/µl) (*Thermus brockianus* from Finnzymes) and 34 µl of water. This mixture was mixed and stored on wet ice. A DNA primer mix was prepared by adding the following to a fresh microcentrifuge tube: 4 µl of 10×repair buffer, 35 µl of captured cDNA from the previous step and 1 µl (50 ng) of unbiotinylated oligo dA-NotI primer. The primer mix was centrifuged at room temperature for 2 sec at 14,000×g and incubated at 95° C. for 1 min. At the same time, the repair mix was incubated at 70° C. The DNA primer mix was transferred to the 70° C. bath and incubated for 1 min. 40 µl of the prewarmed repair mixture was added to the tube containing the DNA primer mix. The contents were mixed by pipetting and then the mixture was incubated at 70° C. for 15 min to allow primer extension (synthesis of double stranded cDNA). The tubes were removed from the water bath and centrifuged at room temperature for 2 s at 14,000×g. The repaired DNA was precipitated by adding 1 µl glycogen, 41 µl of 7.5 M ammonium acetate, and 320 µl of −20° C. ethanol to each tube. The tubes were vortexed and placed in ice for 10 min or at 4° C. overnight. The tubes were then centrifuged at 4° C. for 30 min at 14,000×g. The ethanol was carefully removed from the small pellet and layered with 100 µl of 70% ethanol (−20° C.). The tubes were centrifuged at 4° C. for 2 min at 14,000×g and all of the ethanol was removed and the pellets dried at room temperature for 10 min or until dry. The pellets were dissolved in 10 µl of TE buffer and store at 4° C. 2 µl of aliquots of the repaired DNA was electroporated per 20 µl aliquots of DH10B ElectroMax Competent *E. coli*.

Example 3

Removal of Background from a Normalized cDNA Library Using OligodA-NotI Repair Synthesis with Nucleotide Analogues which Confer Nuclease Resistance Using the approach in Example 2 to remove background, to construct a normalized cDNA library with greater than 1×10$^6$ primary clones minimally requires three independent selections and 15 electroporations (Table 3).

TABLE 3

Comparison of Various Methods to Remove Background.

| Method | Number of Electroporations | Total # of clones | % recombinants |
|---|---|---|---|
| Biotinylated probe selection | 15 3 selections | 1.2 × 10$^6$ | >95% |
| Nuclease resistant repair selection | 5 | 4.8 × 10$^6$ | >95% |

Figure 5:
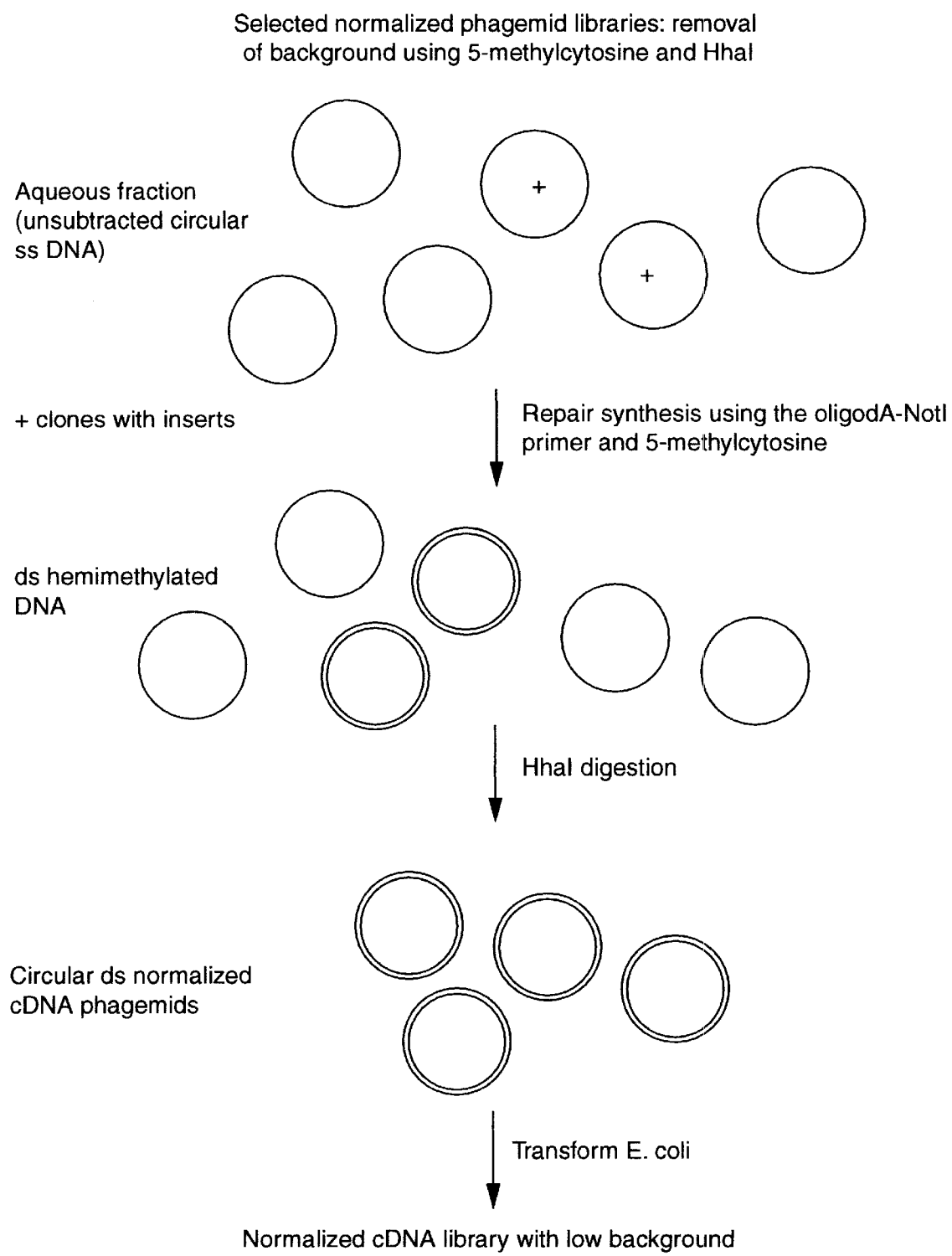
FIG. 5 is a diagram showing how nuclease resistant nucleotides and a nuclease yield low-background normalized phagemid libraries also referred to herein as selected normalized libraries.

To address this issue, an alternative approach was developed to reduce background in normalized libraries. In this method, called nuclease resistant repair synthesis, the same probes described in example 2 is used, oligodA-NotI, but in this case it is not biotinylated (FIG. 5). However, biotinylated probes as used in Example 2 may be used to include the additional selection step of Example 2. When compared to the selection method of Example 2, a library can be constructed that is four times as complex and requires one third the number of electroporations (Table 3). In addition the library background is virtually eliminated and the insert size of the library is unchanged (Table 4). Finally, when highly abundant genes were examined by colony hybridization, their abundance was decreased 15- to 18-fold (Table 5) and the abundance of rare genes was substantially increased (FIG. 6).

TABLE 4

Percent Recombinant cDNA Clones and Average Insert Size Following Total Human Fetal Brain cDNA Library Subtraction and 5-methylcytosine/HhaI Treatment.

| Human Fetal Brain cDNA Library | % recombinants (80 independent clones) | Average insert size (kb) |
|---|---|---|
| Cot = 500 | >95 | 1 |

TABLE 5

Normalized cDNA Library Analysis: Depletion of Abundant cDNAs Depends Directly Upon the Extent of Subtraction.

| Gene | Cot = 0 | Cot = 5 | Cot = 50 | Cot = 500 |
|---|---|---|---|---|
| α-tubulin | 0.78% | 0.62% | 0.24% | 0.043% |
| EF-1α | 0.42% | 0.28% | 0.13% | 0.029% |

Colony hybridization using $^{32}$P-labeled oligonucleotide probes directed to the α-tubulin and elongation factor 1 (EF-1α)

Single-stranded normalized cDNA library generated by subtraction (see Example 1) was repaired as follows: A repair mix was made by combining 3 μl of 10×repair buffer [100 mM Tris-HCl (pH 8.8 at 25° C.), 15 mM MgCl$_2$, 500 mM KCl, 1% Triton X-100], 1 μl 10 mM dNTP (containing 10 mM 5 methyl dCTP), 1 μl of repair enzyme Dynazyme (2 u/μl) (*Thermus brockianus* from Finnzymes) and 25 μl of water, mixing and storing on wet ice. A DNA primer mix for each reaction was made by adding the following to a fresh microcentrifuge tube: 11 μl autoclaved, distilled water, 3 μl of 10×repair buffer, 15 μl of dialyzed DNA from the previous step, and 1 μl (50 ng) of unbiotinylated oligo A-NotI. The mixture was centrifuged at room temperature for 2 sec at 14,000×g. The DNA primer mix was incubated at 95° C. for 1 min. At the same time, the repair mix was incubated at 70° C. The DNA primer mix was transferred to the 70° C. bath and incubated for 1 min. 30 μl of the prewarmed repair mixture was added to the tube containing the primer mix. The contents were mixed by pipetting and incubated at 70° C. for 15 min to allow primer extension (synthesis of double stranded DNA). The tubes were removed from the water bath and centrifuged at room temperature for 2 sec at 14,000×g. The repaired DNA was precipitated by adding 1 μl glycogen, 32 μl of 7.5 M ammonium acetate, and 250 μl of −20° C. ethanol to each tube. The tubes were vortexed and placed in ice for 10 min or at 4° C. overnight. The tubes were then centrifuged at 4° C. for 30 min at 14,000×g. The ethanol was carefully removed from the small pellet and layered with 100 μl of 70% ethanol (−20° C.). The tube was centrifuged at 4° C. for 2 min at 14,000×g. All of the ethanol was removed and the pellets at room temperature for 10 min or until dry. The pellets were dissolved in 10 μl of TE buffer and store at 4° C. The repaired DNA was digested with 0.5 unit of HhaI in 20 μl of 1×buffer (5 mM Tris.HCl, pH 8.0; 1 mM MgCl$_2$; 5 mM NaCl) at 37° C. for 30 min. The DNA was ethanol precipitated and resuspend the dried pellet resuspended in 8 μl of TE. 2 μl aliquots of the repaired DNA was electroporated per 20 μl aliquot of DH10B ElectroMax competent *E. coli*.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for normalization of a nucleic acid library comprising:

(a) synthesizing one or more nucleic acid molecules complementary to all or a portion of the nucleic acid molecules of said library, wherein said synthesized nucleic acid molecules comprise at least one hapten, thereby producing haptenylated nucleic acid molecules;

(b) incubating a nucleic acid library to be normalized with said haptenylated nucleic acid molecules under conditions favoring the hybridization of the more highly abundant molecules of said library with the haptenylated nucleic acid molecules; and (c) removing said hybridized molecules, thereby producing a normalized library.

2. The method of claim 1, wherein said nucleic acid library is a cDNA library.

3. The method of claim 2, wherein the nucleic acid molecules of said cDNA library are single-stranded.

4. The method of claim 2, wherein the nucleic acid molecules of said cDNA library are double-stranded.

5. The method of claim 2, wherein said cDNA library is produced by a method comprising incubating a population of mRNA molecules under conditions sufficient to produce a cDNA library from said population of mRNA molecules.

6. The method of claim 1, wherein said haptenylated nucleic acid molecules are RNA molecules.

7. The method of claim 1, further comprising reduction or removal of contaminating nucleic acid molecules from said library.

8. The method of claim 7, wherein said reduction or removal is performed before or after normalization of said library.

9. The method of claim 7, wherein the contaminating nucleic acid molecules are one or more vectors.

10. The method of claim 7, wherein said reduction or removal comprises incubating said library with at least one haptenylated probe.

11. The method of claim 10, wherein said probe hybridizes to nucleic acid molecules of said library.

12. The method of claim 11, wherein said probe is not capable of hybridizing to vector sequences of said library.

13. The method of claim 10, wherein the haptens of said haptenylated probe are used to isolate a normalized library having substantially reduced contaminating nucleic acid molecules, thereby producing a selected normalized library.

14. The method of claim 13, wherein said haptens are selected from the group consisting of avidin, streptavidin, protein A, protein G, a cell-surface Fc receptor, an antibody-specific antigen, an enzyme-specific substrate, polymyxin B, endotoxin-neutralizing protein (ENP), $Fe^{+++}$, a transferrin receptor, an insulin receptor, a cytokine receptor, CD4, spectrin, fodrin, ICAM-1, ICAM-2, C3bi, fibrinogen, Factor X, ankyrin, an integrin, vitronectin, fibronectin, collagen, laminin, glycophorin, Mac-1, LFA-1, β-actin, gp120, a cytokine, insulin, ferrotransferrin, apotransferrin, lipopolysaccharide, an enzyme, an antibody, biotin and combinations thereof.

15. The method of claim 14, wherein said hapten is biotin.

16. The method of claim 13, wherein said selected normalized library is isolated by hapten-ligand interactions and/or extraction.

17. The method of claim 16, wherein isolation comprises the use of a solid support comprising at least one ligand that binds said hapten.

18. The method of claim 13, wherein said selected normalized library is single-stranded.

19. The method of claim 18, further comprising incubating said single-stranded selected normalized library under conditions sufficient to render said molecules double stranded.

20. The method of claim 19, wherein said conditions comprise incubating said single-stranded selected normalized library with one or more nucleotides, one or more polypeptides having polymerase activity and one or more primers.

21. The method of claim 20, wherein said one or more nucleotides are nucleotide analogues which confer nuclease resistance on said double stranded molecules.

22. The method of claim 21, further comprising digesting a sample comprising said double stranded molecules with said nuclease.

23. The method of claim 22, further comprising transforming said double stranded molecules into one or more host cells.

24. The method of claim 19, further comprising transforming said double stranded molecules into one or more host cells.

25. The method of claim 20, wherein said primers are target specific primers.

26. The method of claim 25, further comprising transforming said double stranded molecules into one or more host cells.

27. The method of claim 6, wherein said RNA molecules are produced by one or more RNA polymerases.

28. The method of claim 27, wherein said RNA polymerases are selected from the group consisting of SP6, T7 and T3 RNA polymerases.

29. The method of claim 6, wherein said RNA molecules are produced with one or more promoters.

30. The method of claim 29, wherein said promoters are provided by one or more vectors or by one or more adapters.

31. The method of claim 30, wherein said promoters allows the synthesis of at least one RNA molecule from all or a portion of the nucleic acid molecules of said library.

32. The method of claim 1, wherein said hybridized molecules are removed by hapten-ligand interactions and/or extraction.

33. The method of claim 32, wherein said removal comprises the use of a solid support comprising at least one ligand.

34. The method of claim 4, further comprising treating said double-stranded cDNA library under conditions sufficient to render said molecules single-stranded.

35. The method of claim 34, wherein said conditions comprise degradation of one strand of said double-stranded molecules.

36. The method of claim 34, wherein said conditions comprise denaturing said double-stranded molecules.

37. The method of claim 35, wherein said degradation is accomplished with gene II and Exonuclease III.

38. The method of claim 1, wherein said hybridization conditions are selected from the group consisting of:

(a) a COT equal to or greater than 25;

(b) a COT equal to or greater than 50;

(c) a COT equal to or greater than 100;

(d) a COT from about 10 to 10,000;

(e) a COT from about 25 to 10,000;

(f) a COT from about 50 to 10,000;

(g) a COT from about 100 to 10,000; and (h) a COT of less than 10,000.

39. The method of claim 7, wherein said reduction or removal comprises incubating said library with at least one primer and at least one nucleotide which confers nuclease resistance under condition sufficient to make double stranded nucleic acid molecules.

40. The method of claim 39, wherein said primer hybridizes to nucleic acid molecules of said library.

41. The method of claim 39, wherein said primer is not capable of hybridizing to vector sequences of said library.

42. The method of claim 39, wherein said nucleotide is a nucleotide analog.

43. The method of claim 42, wherein said nucleotide analog is a methylated nucleotide.

44. The method of claim 43, wherein said methylated nucleotide is 5-methyldeoxycytosine.

45. The method of claim 39, further comprising digesting said double-stranded nucleic acid molecules with one or more nucleases.

46. The method of claim 45, further comprising transforming said digested molecules into one or more host cells.

47. A normalized nucleic acid library produced by the method of claim 1.

48. A selected normalized library produced by the method of claim 7.

49. A transformed host cell produced by the method of claim 23.

50. A transformed host cell produced by the method of claim 24.

51. A transformed host cell produced by the method of claim 26.

52. A transformed host cell produced by the method of claim 46.

* * * * *

SEQUENCE LISTING

```
<160> NUMBER OF SEQ ID NOS: 2

<210> SEQ ID NO 1
<211> LENGTH: 48
<212> TYPE: DNA
<213> ORGANISM: Artificial sequence
<220> FEATURE:
<223> OTHER INFORMATION: Description of artificial  sequence: synthetic
      oligonucleotide

<400> SEQUENCE: 1
gaaggtacgc ctgcaggtac cggtccggaa ttcccgggtc gacccacg                48

<210> SEQ ID NO 2
<211> LENGTH: 25
<212> TYPE: DNA
<213> ORGANISM: Artificial sequence
<220> FEATURE:
<223> OTHER INFORMATION: Description of artificial  sequence: synthetic
      oligonucleotide

<400> SEQUENCE: 2
aaaaaaaaaa aaaaagggcg gccgc                                         25
```